(12) United States Patent
Peshkova et al.

(10) Patent No.: US 8,790,591 B2
(45) Date of Patent: Jul. 29, 2014

(54) IN VITRO POINT-OF-CARE SENSOR AND METHOD OF USE

(75) Inventors: Maria Peshkova, Cleveland, OH (US); Armand Krikorian, Richmond Heights, OH (US); Sumitha Nair, Cleveland, OH (US); Punkaj Ahuja, Cleveland, OH (US); Miklos Gratzl, Mayfield Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 13/809,318

(22) PCT Filed: Jul. 11, 2011

(86) PCT No.: PCT/US2011/043583
§ 371 (c)(1),
(2), (4) Date: Jan. 9, 2013

(87) PCT Pub. No.: WO2012/021239
PCT Pub. Date: Feb. 16, 2012

(65) Prior Publication Data
US 2013/0109040 A1    May 2, 2013

Related U.S. Application Data

(60) Provisional application No. 61/362,962, filed on Jul. 9, 2010.

(51) Int. Cl.
*G01N 33/52* (2006.01)
(52) U.S. Cl.
USPC ........... 422/430; 422/417; 422/421; 422/426; 422/401

(58) Field of Classification Search
CPC ..... G01N 21/253; G01N 21/66; G01N 21/76; G01N 2201/0446; G01N 35/028
USPC .......................................... 422/430
See application file for complete search history.

(56) References Cited

U.S. PATENT DOCUMENTS

| | | | |
|---|---|---|---|
| 5,525,475 A * | 6/1996 | Ladouceur | 435/7.9 |
| 2003/0132406 A1* | 7/2003 | Waldhausl et al. | 250/574 |
| 2007/0056858 A1 | 3/2007 | Chen et al. | |
| 2009/0260985 A1 | 10/2009 | Wang et al. | |
| 2010/0012511 A1 | 1/2010 | Heller et al. | |

\* cited by examiner

*Primary Examiner* — Sally Merkling
(74) *Attorney, Agent, or Firm* — Tarolli, Sundheim, Covell & Tummino LLP

(57) ABSTRACT

An in vitro sensor for point-of-care detection of at least one analyte or reaction product includes an inert, impermeable substrate, a sensing system, and a reference system. The substrate includes a first transparent surface oppositely disposed from a second surface and first and second cavities. Each of the first and second cavities defines an opening at the second surface. The sensing system is disposed in at least a portion of the first cavity and includes an analyte-detection optode membrane, an analyte-permeable membrane, and a plurality of non-transparent microbeads associated with at least one of the analyte-detection optode membrane and the analyte-permeable membrane. The analyte-permeable membrane is layered upon the analyte-detection optode membrane and covers the opening of the first cavity. The reference system is disposed in at least a portion of the second cavity.

18 Claims, 29 Drawing Sheets

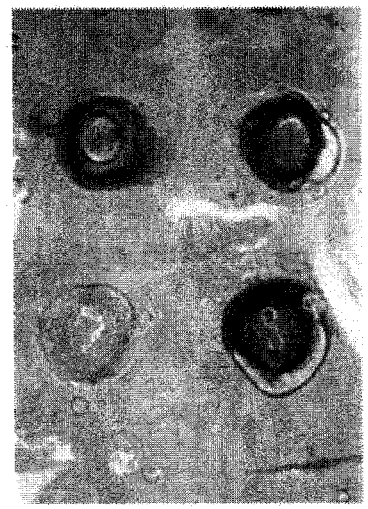
Fig. 31
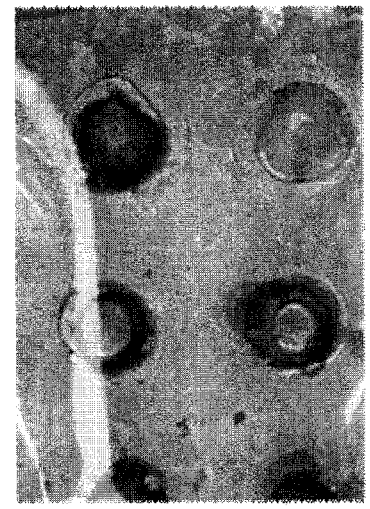

IN VITRO POINT-OF-CARE SENSOR AND METHOD OF USE

RELATED APPLICATIONS

This application is a continuation-in-part of, and claims priority to, U.S. patent application Ser. No. 13/112,018, filed May 20, 2011, which is a divisional of U.S. Pat. No. 7,964,390, filed Feb. 2, 2005, which claims priority to U.S. Provisional Patent Application Ser. No. 60/541,418, filed Feb. 3, 2004 (now Expired), and is continuation-in-part of U.S. patent application Ser. No. 10/683,315, filed Oct. 10, 2003 (now Abandoned), which claims priority to U.S. Provisional Patent Application Ser. Nos. 60/501,066, filed Sep. 8, 2003 (now Expired), 60/444,582, filed Feb. 3, 2003 (now Expired), and 60/417,971, filed Oct. 11, 2002 (now Expired), and 61/362,962, filed Jul. 9, 2010, the entireties of all of which are hereby incorporated by reference.

FIELD OF THE INVENTION

The present invention relates to in vitro sensors, and more particularly to in vitro sensors for point-of-care testing of metabolic profiles.

BACKGROUND OF THE INVENTION

The metabolic status of critically ill patients in the intensive care unit (ICU) is of critical importance and needs frequent monitoring. For example, glycemic control in critically ill patients has been shown to positively impact both morbidity and mortality. This has been shown to be true whether the patients have preexisting diabetes or not. Current standards of care for hyperglycemic patients in the intensive care setting involve the use of insulin infusion and monitoring of blood glucose at regular intervals (e.g., once every hour, 24 hours a day).

Metabolic monitoring in most patients is restricted to measuring glucose in blood drawn with a finger prick and then analyzing the sample using commercially available electrochemical glucose monitors, such as the ONETOUCH (LifeScan, Inc., Milpitas, Calif.) or ACCU-CHEK (Roche Diagnostics Corp., Indianapolis, Ind.) systems. Hypoglycemia is the most common complication of using insulin infusion, while also the most limiting and potentially detrimental to patient safety. Yet, the commercially available meters' accuracy decreases significantly at blood glucose levels within the hypoglycemia range (i.e., below 60 mg/dl).

The only metabolic parameter that commercially available glucometers can determine is blood glucose. The monitoring of other fundamental parameters, such as pH, bicarbonate, $K^+$, or lactate is also desirable in a number of situations. Specifically, shifts in potassium between the intracellular and extracellular space are known to occur with insulin therapy. Since sepsis and respiratory failure are common reasons for admission to the ICU, frequent bedside pH measurements are needed and currently performed by arterial blood sampling and blood gas analysis in a central laboratory. This, along with the numerous disposable test strips required for patient care, increases the already high costs of care in the ICU.

SUMMARY OF THE INVENTION

In accordance with one aspect of the present invention, an in vitro sensor for point-of-care (POC) detection of at least one analyte or reaction product comprises an inert, impermeable substrate, a sensing system, and a reference system. The substrate includes a first transparent surface oppositely disposed from a second surface and first and second cavities. Each of the first and second cavities defines an opening at the second surface. The sensing system is disposed in at least a portion of the first cavity and comprises an analyte-detection optode membrane, an analyte-permeable membrane, and a plurality of non-transparent microbeads associated with at least one of the analyte-detection optode membrane and the analyte-permeable membrane. The analyte-permeable membrane is layered upon the analyte-detection optode membrane and covers the opening of the first cavity. The reference system is disposed in at least a portion of the second cavity.

In accordance with another aspect of the present invention, a method is provided for detecting at least one analyte or reaction product in a biological fluid sample taken from a subject at a POC. One step of the method includes providing an in vitro sensor comprising a substrate, a sensing system, and a reference system. The substrate includes first and second cavities. The sensing system is at least partially disposed in the first cavity, and the reference system is at least partially disposed in the second cavity. The sensing system comprises an analyte-detection optode membrane, an analyte-permeable membrane, and a plurality of non-transparent microbeads associated with at least one of the analyte-detection optode membrane and the analyte-permeable membrane. The analyte-permeable membrane is layered upon the analyte-detection optode membrane and covers the opening of the first cavity. After providing the sensor, the biological fluid sample is obtained from the subject and contacted with at least a portion of the analyte-permeable membrane. Next, a color change is detected within the sensing system.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 31 is a series of images showing glucose sensor (FIG. 24) response in blood with varying glucose concentrations (a: 0 mg/dL, b: 100 mg/dL, c: 200 mg/dL).

DETAILED DESCRIPTION

Figure 1A:
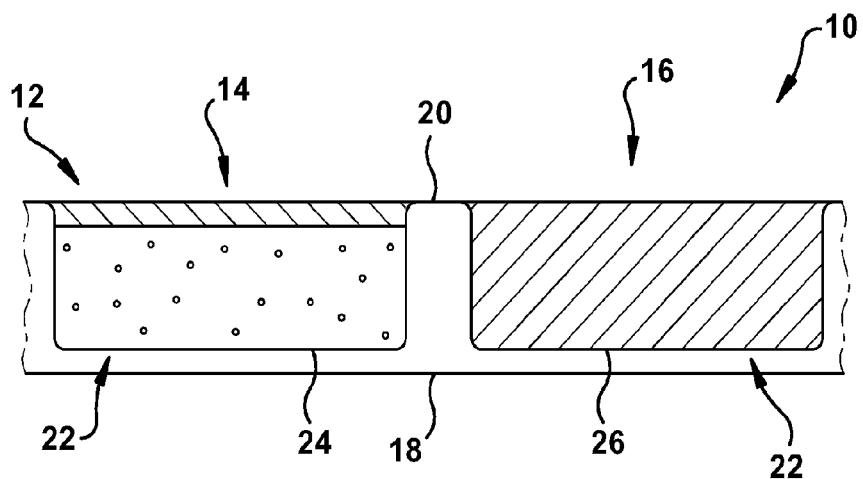
FIG. 1A is a cross-sectional view of an in vitro sensor comprising a substrate, a sensing system for point-of-care (POC) detection of at least one analyte or reaction product, and a reference system constructed in accordance with one aspect of the present invention.
Figure 1B:
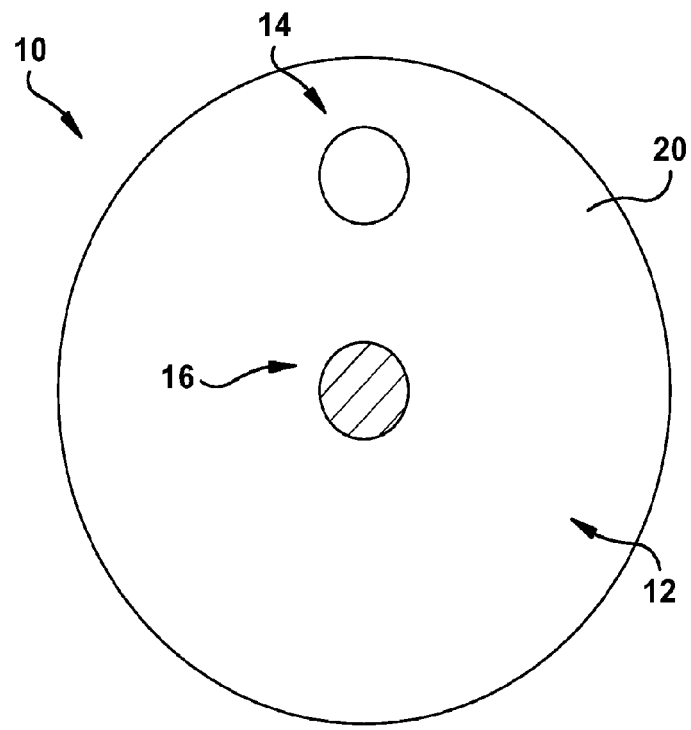
FIG. 1B is a top view of the sensor shown in FIG. 1A.

The present invention relates to in vitro sensors, and more particularly to in vitro sensors for point-of-care (POC) testing of metabolic profiles. As illustrative of one aspect of the present invention, FIGS. 1A-B show an in vitro sensor 10 for POC testing of metabolic profiles comprising a substrate 12, a sensing system 14 for detecting at least one analyte or reaction product, and a reference system 16. The in vitro sensor 10 of the present invention provides a snapshot of the overall metabolic status of a subject from a single drop of blood in real-time. Since the sensor 10 is reversible and requires no reagents to operate, only one sensor can be reused many times so that an individual subject's entire period of care in a critical care environment (e.g., an intensive care unit or ICU) is covered with a single sensor. This is unlike current test strip-based electrochemical technologies used to measure analytes (e.g., glucose) from blood samples, in which each strip must be disposed of after a single measurement. Advantageously, the present invention provides a simple, integrated, and reusable in vitro sensor 10 that can use the same biological fluid sample (e.g., a droplet of blood) for measuring a number of vital metabolic parameters in parallel at a POC to enable better metabolic control of critically ill subjects.

One aspect of the present invention can include an in vitro sensor 10 for POC testing of metabolic profiles comprising a substrate 12, a sensing system 14 for detecting at least one analyte or reaction product, and a reference system 16. The shape and dimensions of the sensor 10 are not critical and can vary depending on the fabrication method or intended application of the sensor. For example, the sensor 10 can have a circular shape with a diameter of about 5 mm. It will be appreciated that the sensor 10 can have other shapes, such as rectangular, square, ovoid etc. The sensor 10 can be fabricated by one or a combination of fabrication techniques, such as microfabrication and MEMS technologies. These techniques may be combined with one or more electrochemical techniques, membrane fabrication technology, enzyme and/or optical dye immobilization, etc. to fabricate the sensor 10.

As shown in FIGS. 1A-B, the substrate 12 can include a first surface 18 oppositely disposed from a second surface 20. All or a portion of the first surface 18 may be transparent. As discussed in more detail below, this allows the color change (s) of the sensing system 14 to be visible through the substrate 12. Alternatively, all or a portion of the substrate 12 may have an opaque, reflective, or colored surface to provide contrast for the color change(s) of the sensing system 14. The substrate 12 can be formed from one or a combination of inert and impermeable materials, such as plastic, glass, ceramic, or the like. For example, the substrate 12 can be formed from one or more of polymethylmetacrylate (PMMA), 2-hydroxyethyl methacrylated (HEMA), or glass. In one example of the present invention, the substrate 12 can be formed from glass.

The substrate 12 can also include a plurality of cavities 22. For example, the substrate 12 can include first and second cavities 24 and 26, each of which defines an opening 28 at the second surface 20. Although the first and second cavities 24 and 26 are shown in FIG. 1B as having a circular cross-sectional shape, it will be appreciated that the cavities can have other cross-sectional shapes (e.g., ovoid, square, etc.). The dimensions of the first and second cavities 24 and 26 can be varied as needed. For the first and second cavities 24 and 26 shown in FIGS. 1A-B, for instance, each of the cavities can have a diameter of about 1 mm and a depth of about 300 µm. The first cavity 24 and/or the second cavity 26 may have white or mirrored bases and be formed by drilling (e.g., with a laser), etching, or the like. Depending upon the particular application for which the sensor 10 is intended, it will be appreciated that any number of cavities 22 can be included in the substrate 12.

Figure 2A:
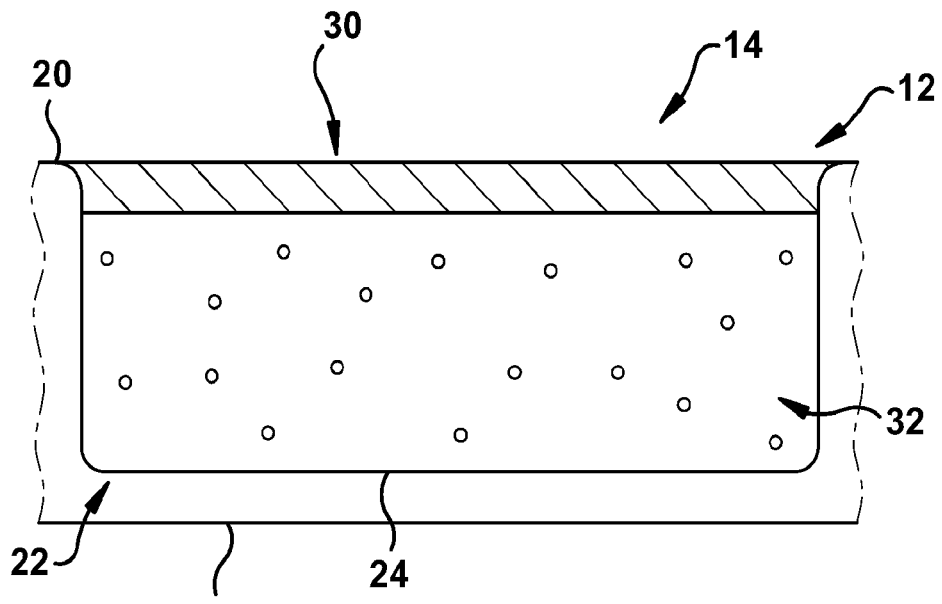
FIG. 2A is a magnified cross-sectional view of the sensing system shown in FIG. 1A.

In another aspect of the present invention, the sensor 10 can comprise a sensing system 14 for detecting at least one analyte or reaction product. As shown in FIG. 2A, the sensing system 14 can be at least partially disposed in the first cavity 24 of the substrate 12. Generally, the sensing system 14 is capable of sensing or detecting an optical property, such as a color change of an absorption dye or emission by a fluorescent dye that changes with changing concentration of the analyte or reaction product.

The sensor 10 can include any number and variety of sensing systems 14. These include sensing systems 14 for the detection of glucose, lactate, oxygen, urea, creatinin, bicarbonate, potassium, sodium, and other biochemical species. For example, the enzyme glucose oxidase may be used for the detection of glucose, the enzyme lactase may be used for detection of lactose, the enzyme galactose oxidase may be used for the detection of galactose, the enzyme urate oxidase may be used for the detection of uric acid, and the enzyme creatinine amidhydrogenase may be used for the detection of creatinine. Sensing systems 14 for the detection of pH, temperature, vital ions, such as K+, Na+, and the like, may also be included in the sensor 10.

Multiple sensing systems 14 may be provided for a single analyte or reaction product to provide redundancy or to provide for different sensitivity ranges, e.g., a first sensing system for high concentrations and a second sensing system for low concentration ranges. Sensing systems 14 for different analytes or reaction products may be accommodated in a single sensor 10. A number of different sensing systems 14 may thus be associated with a single sensor 10.

As shown in FIG. 2A, the sensing system 14 can comprise an analyte-detection optode membrane 30, an analyte-permeable membrane 32, and at least one non-transparent microbead 34 that is in contact with at least one of the analyte-detection optode membrane or the analyte-permeable membrane. The analyte-detection optode membrane 30 can be disposed in the first cavity 24 and comprise a matrix material, such as a plasticized polymer (e.g., plasticized PVC). As described in more detail below, the analyte-detection optode membrane 30 does not function based on any binding equilibrium; rather, the analyte-detection optode membrane functions based on charge balance between ions that are taken up or released. The sensing system 14 can transduce ionic concentrations indicated by the analyte-detection optode membrane 30 into analyte concentration.

The analyte-detection optode membrane 30 can generally include one or more indicator materials, such as a pH sensitive dye that undergoes a chemical or physical change in response to an analyte to be detected or to a reaction product thereof. Additionally, the analyte-detection optode membrane 30 can include one or more detection materials. In general, the detection material can react with an analyte or catalyze a reaction of an analyte to produce a detectable reaction product. Or, the reaction/catalysis can result in an intermediate reaction product that undergoes further reaction/catalysis with a second or subsequent detection material to form a detectable product. For example, a first detection material can react with or catalyze the reaction of an analyte to produce an intermediate reaction product. A second detection material can then react with or catalyze the reaction of the intermediate reaction product to produce a detectable product.

The detection material can generally comprise an enzyme that reacts with the analyte and/or catalyses the reaction of an analyte to produce a detectable reaction product. In the case of glucose, for example, glucose oxidase, glucose dehydrogenase, or another enzyme that catalyses a reaction of glucose can be employed as the detection material. Additionally, in the case of lactate detection, lactase may be used.

The indicator material, as mentioned above, may be a pH sensitive material (e.g., a dye) that is responsive to a pH change induced by an analyte or, more commonly, a detectable product by producing a color change (i.e., a change in the absorption wavelength, which may include wavelengths outside the visible range, such as in the IR range), fluorescence, or the like. The color change is reversible, depending upon the concentration of the analyte(s). Exemplary indicator materials, such as dyes can include Congo red, neutral red, phenol red, methyl red, lacmoid, tetrabromophenolphthalein, α-naphtholphenol, and the like. A dye may be dissolved in organic solvent, such as (NPOE (2-nitrophenyl octyl ether), BEHS (bis(2-ethylhexyl)sebacate), DBE (dibenzyl ether), DOP (dioctyl phthalate), or the like.

In one example of the present invention, the indicator material can comprise a light-absorbing, pH-sensitive dye that undergoes a color change in response to an analyte or a reaction product thereof. For instance, the indicator material can comprise a dye that is sensitive to hydrogen ions (i.e., pH) and is reversible (i.e., returns to its previous color when the pH returns to its previous level). Examples of pH-sensitive dyes can generally include ionophores, lipophilic anions, and lipophilic hydrogen ion sensitive dyes (also referred to herein as a chromoionophores). It will be appreciated that where ions other than hydrogen are to be detected, other dyes may be used. Generally, the method of using a lipophilic hydrogen ion sensitive dye in combination with an ionophore together in a solvent or membrane is referred to herein as an optode technique. In such an arrangement, the ionophore can extract the ion to be detected and the lipophilic hydrogen sensitive dye can exhibit a corresponding color change.

By optimizing the composition of a pH-sensitive optode membrane, the maximum color change can be obtained in the desired pH range, typically from about pH 5.0 to 8.0 in the presence of an electrolyte at concentrations that are approximately equal to those in a biological fluid sample (e.g., blood or serum).

Exemplary chromoionophores can include one or more of:
chromoionophore I (9-(diethylamino)-5-(octadecanoylimino)-5H-benzo[a]phenoxazine), designated ETH5249;
chromoionophore II (9-dimethylamino-5-[4-(16-butyl-2,14-dioxo-3,15 ioxaeicosyl)phenylimino]benzo[a]phenoxazine), designated ETH2439;
chromoionophore III (9-(diethylamino)-5-[2-octyldecyl)imino]benzo[a]phenoxazine), designated ETH 5350;
chromoionophore IV (5-octadecanoyloxy-2-(4-nitrophenylazo)phenol), designated ETH2412;

chromoionophore V (9-(diethylamino)-5-(2-naphthoylimino)-5H-benzo[a]phenoxazine);
chromoionophore VI (4',5'-dibromofluorescein octadecyl ester), designated ETH7075;
chromoionophore XI (fluorescein octadecyl ester), designated ETH7061; and combinations thereof (note that ETF is the designation of the Swiss Federal Institute of Technology).

Examples of lipophilic anions can include KTpClPB (potassium tetrakis(4-chlorophenyl)borate), NaHFPB (sodium tetrakis[3,5-bis(1,1,3,3,3-hexafluoro-2-methoxy-2-propyl)phenyl]borate), sodium tetrakis[3,5-bis(trifluoromethyl)phenyl]borate, sodium tetrakis(4-fluorophenyl)borate, combinations thereof, and the like.

Ionophores can include sodium ionophores, potassium ionophores, calcium ionophores. Examples of sodium ionophores can include:
  bis[(12-crown-4)methyl]2-dodecyl-2-methylmalonate, designated ETH227;
  N,N',N'''-triheptyl-N,N',N'''-trimethyl4,4',4''-propylidynetris(3-oxabutyramide), designated ETH157;
  N,N'-dibenzyl-N,N'-diphenyl-1,2-phenylenedioxydiacetamide, designated ETH2120;
  N,N,N',N'-tetracyclohexyl-1,2-phenylenedioxydiacetamide, designated ETH4120;
  4-octadecanoyloxymethyl-N,N,N',N'-tetracyclohexyl-1,2-phenylenedioxydiacetamide), designated DD-16-C-5;
  2,3:11,12-didecalino-16-crown-5), bis(benzo-15-crown-5); and combinations thereof.

Examples of potassium ionophores can include:
  bis[(benzo-15-crown-5)-4'-methyl]pimelate, designated BME 44;
  2-dodecyl-2-methyl-1,3-propanedil bis[N-{5'-nitro(benzo-15-crown-5)-4'-yl]carbamate], designated ETH1001; and combinations thereof.

Examples of calcium ionophores can include:
  (−)-(R,R)—N,N'-bis-[11-(ethoxycarbonyl)undecyl]-N,N'-4,5-tetramethyl-3,6-dioxaoctane-diamide), designated ETH129;
  N,N,N',N'-tetracyclohexyl-3-oxapentaned iamide, designated ETH5234;
  N,N-dicyclohexyl-N',N'-dioctadecyl-3-oxapentanediamide), designated K23E1;
  10,19-bis[(octadecylcarbamoyl)methoxyacety]-1-1,4,7,13,16-pentaoxa-10,19-diazacycloheneicosane); and combinations thereof.

In one example of the present invention, the analyte-detection optode membrane 30 can have the following composition: about 50 mmol of chromoionophore ETH5350 (L); about 360 mmol sodium ionophore Na IV (I); about 55 mmol NaHFPB; and about 0.65 polyvinylchloride:bis(2-ethylhexyl)sebacate. In this case, the equilibrium of such an analyte-detection optode membrane 30 can be represented by the following equation:

$$L^{(m)}+INa^{+(m)}+H^+ \leftrightarrow LH^{+(m)}+I^{(m)}+I^{(m)}+Na^{+(aq)}.$$

Figure 2B:
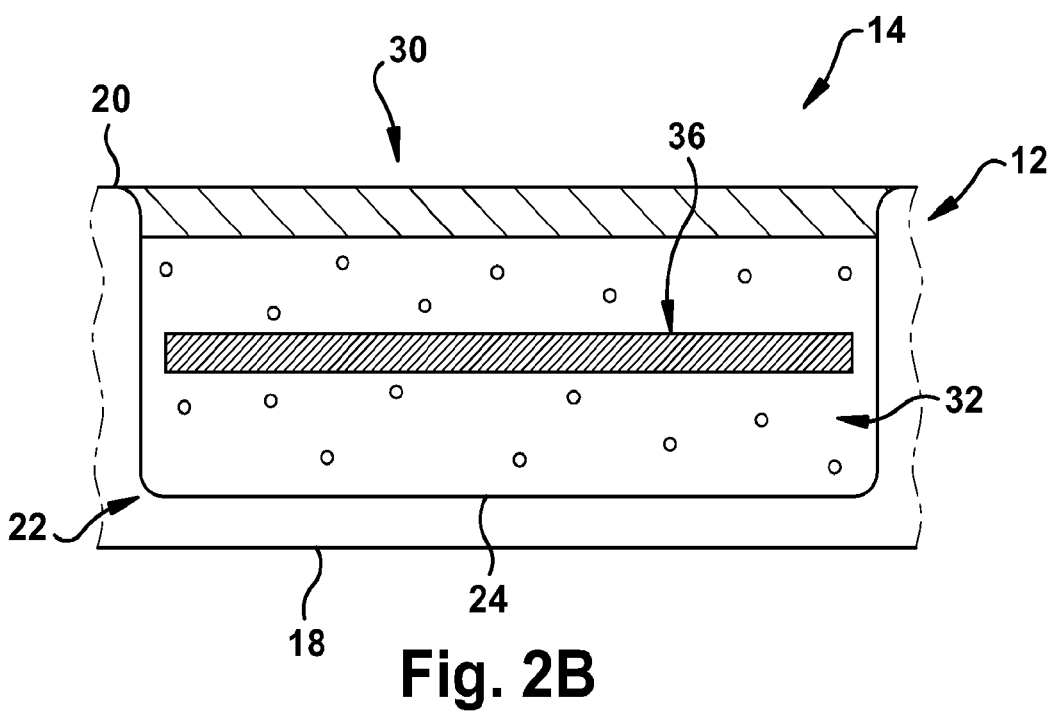
FIG. 2B is a magnified cross-sectional view showing an alternative embodiment of the sensing system in FIG. 2A.

In another example of the present invention, the analyte-detection optode membrane 30 can be configured to detect the presence and/or concentration of glucose. The analyte-detection optode membrane 30 can generally comprise, for example, a plasticized polymer, a chromoionophore, an ionophore, and a lipophilic anion. As shown in FIG. 2B, the analyte-detection optode membrane 30 can further comprise an enzyme-loaded membrane 36, such as a glucose oxidase-loaded membrane. In the glucose oxidase-loaded membrane 36, the following enzyme reaction can occur:

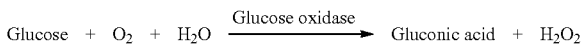

$$\text{Glucose} + O_2 + H_2O \xrightarrow{\text{Glucose oxidase}} \text{Gluconic acid} + H_2O_2$$

Because the above enzyme reaction produces gluconic acid, the pH in the analyte-detection optode membrane 30 changes with changing concentration of glucose. The color (i.e., the absorption spectrum) of the pH indicator dye present in or on the enzyme-loaded membrane 36 or the analyte-detection optode membrane 30 will change due to the pH change in the membrane(s). It is this change in the spectrum that is detected and used to determine glucose concentration. Advantageously, such a glucose sensing system can detect glucose in the hypoglycemic range (e.g., below about 60 mg/dl).

Figure 3A:
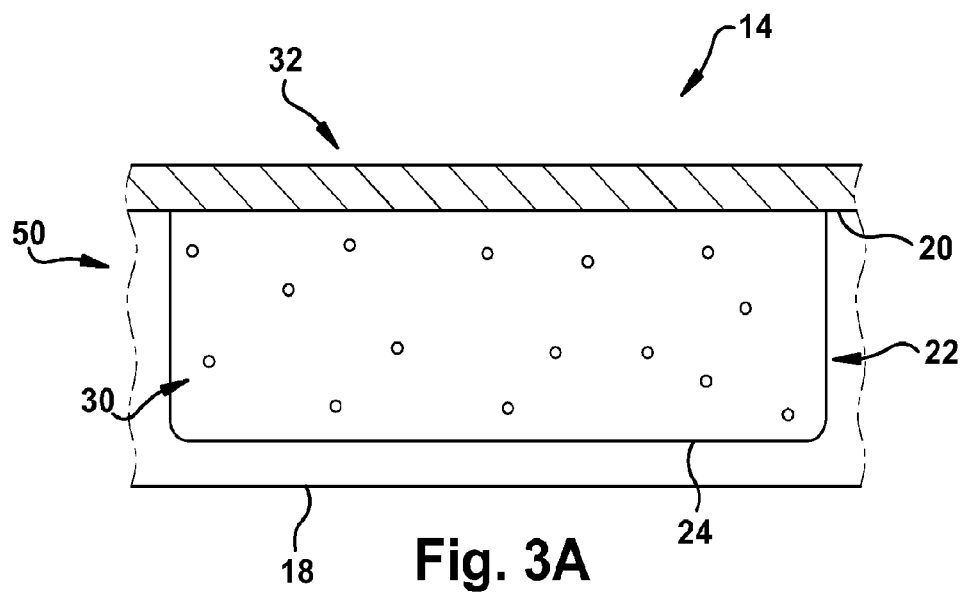
FIG. 3A is a magnified cross-sectional view of the sensing system in FIG. 1A showing an alternative configuration of an analyte-permeable membrane (cross-hatched region)

In another aspect of the present invention, the analyte-permeable membrane 32 can be layered upon the analyte-detection optode membrane 30 and cover the opening 28 of at least the first cavity 24. Generally, the analyte-permeable membrane 32 can comprise one or more substantially hydrophilic layers that is/are permeable to select molecules and provide(s) both protective and functional roles. For example, the analyte-permeable membrane 32 can be layered upon the analyte-detection optode membrane 30 to simultaneously retain the analyte-detection optode membrane within the first cavity 24 and protect the analyte-detection optode membrane from damage. All or a portion of the analyte-permeable membrane 32 can be transparent. As shown in FIGS. 2A-B, the analyte-permeable membrane 32 can be disposed within the first cavity 24; however, it will be appreciated that the analyte-permeable membrane may alternatively extend across the second surface 20 of the substrate 12 (i.e., covering at least the opening 28 of the first cavity 24) and, optionally, the openings of other cavities 22 (FIG. 3A).

Functionally, the analyte-permeable membrane 32 can control the diffusion of target analyte(s) and thereby lead to the improvement of linearity and dynamic range of the sensor's 10 response (e.g., provide higher sensitivity and selectivity). For example, the analyte-permeable membrane 32 can exclude anions, cations, lipids, and/or proteins. The composition of the analyte-permeable membrane 32 can affect diffusion of charged ions into the first cavity 24. For example, phosphate ions from a biological fluid sample can diffuse through the analyte-permeable membrane 32 and thereby increase the buffering capacity of the sensing system 14. If the diffusion rate is slowed by selection of the materials used to form the analyte-permeable membrane 32, the buffering capacity within the first cavity 24 can be maintained at a low level and, thus, sensitivity can be increased. The composition of the analyte-permeable membrane 32 can also affect the response time of the sensing system 14. For example, high analyte permeability can allow for a very short response time.

In one example of the present invention, analyte-permeable membrane 32 can comprise a negatively-charged hydrophilic gel, which includes at least one polyanion to reduce the buffering capacity of the sensing system 14. Buffer capacity is the ability of the components of the sensing system 14 to buffer the pH of a medium. When the buffer capacity is high, more acid is required to lower the pH than is the case when the buffer capacity is low. As a consequence, detection systems that are based on a change in pH become less sensitive. Where there is a large buffering capacity, the pH change is minimized and the system is less sensitive (e.g., it takes more acid to achieve a certain pH change). An analyte-permeable member 32 comprising a negatively-charged hydrophilic gel thus allows the sensitivity of the sensing system 14 to be adjusted.

As mentioned, the structure of the analyte-permeable membrane 32 also permits control of the diffusion of analyte species across the analyte-permeable membrane, which allows the sensitivity of the sensing system to be controlled. For example, if low glucose concentrations are to be measured, the analyte-permeable membrane 32 (and/or other aspects of the sensing system 14) can be designed to be particularly sensitive. If high glucose concentration is to be measured, a lower sensitivity may be desired. The sensitivity of the analyte-permeable membrane 32 to glucose concentration can be controlled, for example, by modifying the relative hydrophobicity of the analyte-permeable membrane.

Depending upon the protective and/or functional characteristics desired, the analyte-permeable membrane 32 can be formed from any one or combination of polymeric, matrix-forming, and/or hydrogel materials. For example, the analyte-permeable membrane 32 can be comprised of any one or combination of positively-charged cellulose, negatively-charged cellulose, BSA-glutaraldehyde, PEG, chitosan, cellulose acetate (CA) or cellulose acetate phthalate (CAP)-heparin, chitosan-heparin, polyurethane, polyvinyl pyrrolidone, acrylic polyester, fluorocarbons, silicone rubber, agar, HEMA, and the like. In one example of the present invention, the analyte-permeable membrane 32 can comprise a polyurethane film.

Figure 3B:
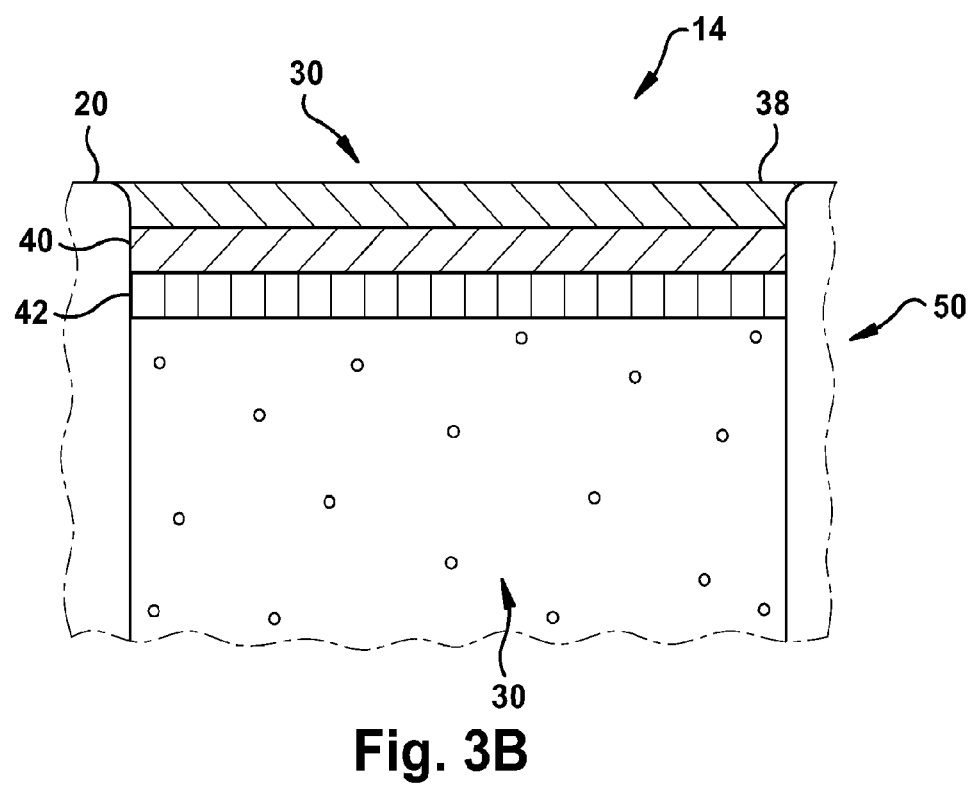
FIG. 3B is a cross-sectional view of the sensing system in FIG. 3A showing an alternative configuration of the analyte-permeable membrane having a multi-layered configuration.

The analyte-permeable membrane 32 can have a multilayered structure. As shown in FIG. 3B, for example, the analyte-permeable membrane 32 can comprise three layers: an outermost layer 38; a middle layer 40; and an inner layer 42. The outermost layer 38, which is exposed to a biological fluid sample, can function as a protective layer and have a thickness of about 2-3 µm. The middle layer 40 can function to regulate and limit the diffusion of an analyte (or analytes) into the first cavity 24 and be formed, for example, from polyurethane, polyvinylpyrrolidone, acrylic polyesters, vinyl resins, fluorocarbons, silicones, rubbers, HEMA, or combinations thereof. Polyurethane, for example, can be effective in slowing glucose diffusion relative to that of oxygen and downgrading glucose levels to below the Michaelis-Menten constant, rendering the overall response nearly linear. The middle layer 40 can have a thickness of about 5-20 µm.

The inner layer 42 can comprise a negatively-charged layer to reduce the efflux of a reaction product (e.g., gluconic acid) from inside of the first cavity 24. This control can lead to a further improvement in glucose sensitivity due to the reduction in gluconic acid efflux via the negatively-charge membrane 42. The inner layer 42 may be formed from one or a mixture of polymer and/or matrix-forming materials, such as CA and CAP according to the desired sensitivity of the sensing system 14. In one example of the present invention, the inner layer 42 can be formed from a combination of CA and CAP in a ratio that allows the diffusion rate of charged ions into and/or out of the first cavity 24 to be controlled. For example, phosphate ions can diffuse through the inner layer 42, increasing buffering capacity. If the diffusion rate is slowed by selection of inner layer 42 materials, the buffering capacity within the first cavity 24 can be maintained at a low level and sensitivity is increased. The diffusion rate, and hence sensitivity, can thus be controlled by changing the ratio of CA to CAP in the inner layer 42.

In another aspect of the present invention, the sensing system 14 can comprise at least one substantially non-transparent microbead 34 (FIGS. 4A-C), or other discrete substantially non-transparent particle. One or more microbeads 34 can be colored and/or made from one or a combination of materials to facilitate diffuse reflectance within the sensing system 14. To facilitate diffuse reflectance, the microbeads 34 can filter out the color of an underlying biological fluid sample (e.g., serum or blood). The microbeads 34 may have the same or different average diameters. For example, one or more microbeads 34 can have an average diameter of about 0.5-100 µm. It will be appreciated that not all of the microbeads 34 need be non-transparent; rather, only a sufficient number of the microbeads need be non-transparent to facilitate diffuse reflectance.

One or more of the microbeads 34 can be comprised of one or combination of materials to facilitate diffuse reflectance. For example, one or more of the microbeads 34 can be made from PVC, CA, CAP, glass, Teflon, and/or a combination thereof. It will be appreciated that all of the microbeads 34 can be formed from the same material or, alternatively, at least one of the microbeads can be formed from a material different than the material used to form the other microbeads.

Figure 4A:
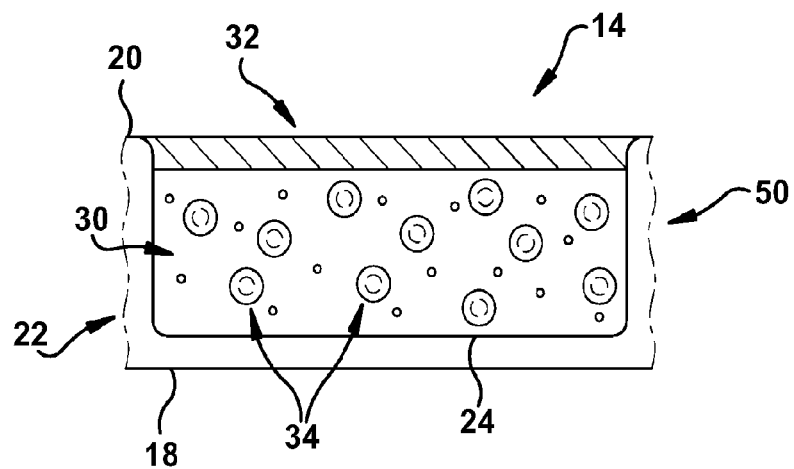
FIG. 4A is a magnified cross-sectional view showing an alternative embodiment of the sensing system in FIG. 1A including a plurality of microbeads dispersed throughout an analyte-detection optode membrane (dotted region)
Figure 4B:
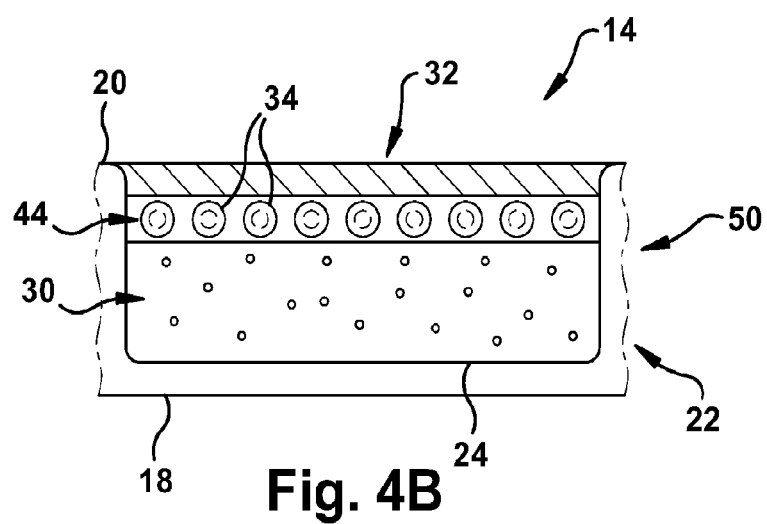
FIG. 4B is a magnified cross-sectional view showing an alternative embodiment of the sensing system in FIG. 4A.
Figure 4C:
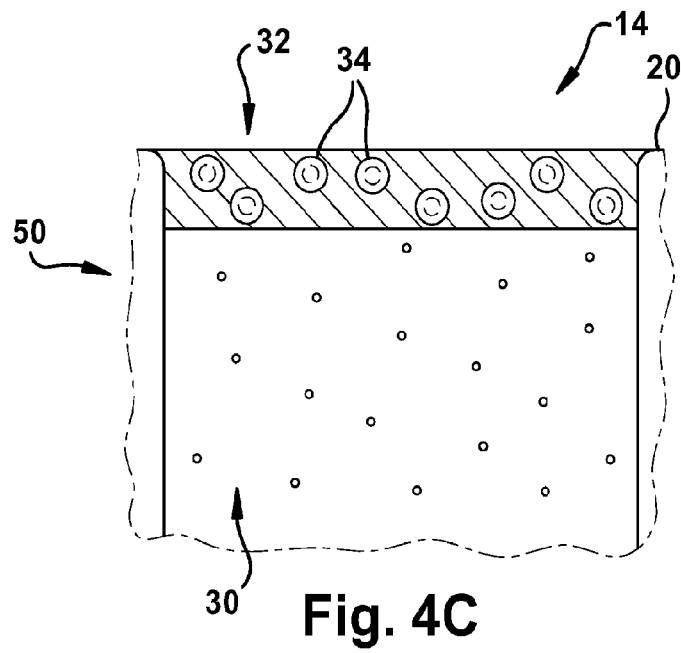
FIG. 4C is a magnified cross-sectional view showing another alternative embodiment of the sensing system in FIG. 4A.

The microbeads 34 can be in contact with at least one of the analyte-permeable membrane 32 and the analyte-detection optode membrane 30. As shown in FIG. 4A, for example, the microbeads 34 can be dispersed (e.g., randomly or uniformly) throughout the analyte-detection optode membrane 30. Alternatively, the microbeads 34 can be formed into a layer 44 (FIG. 4B). The layer 44 of microbeads 34 can be comprised entirely of microbeads or, optionally, include a support material (e.g., PEG) for suspending the microbeads therein. The microbeads 34 may also be dispersed (e.g., uniformly or randomly) throughout the analyte-permeable membrane 32. In one example of the present invention, a plurality of glass microbeads 34 can be dispersed throughout an analyte-permeable membrane 32 comprised of polyurethane.

Figure 5A:
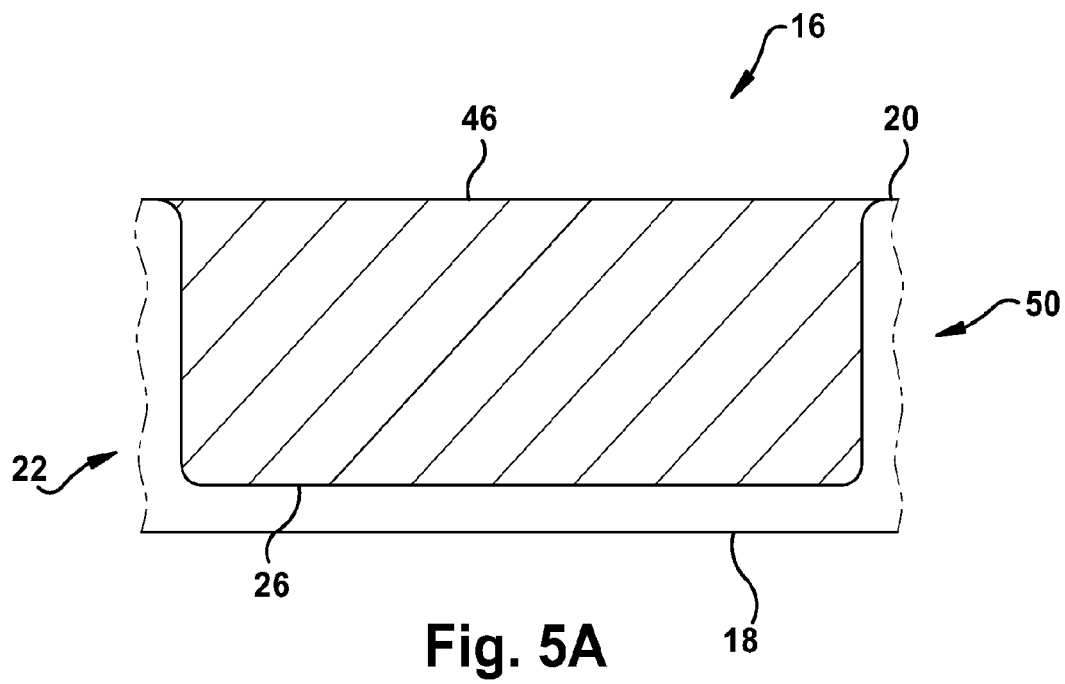
FIG. 5A is a magnified cross-sectional view of the reference system in FIG. 1A.
Figure 5B:
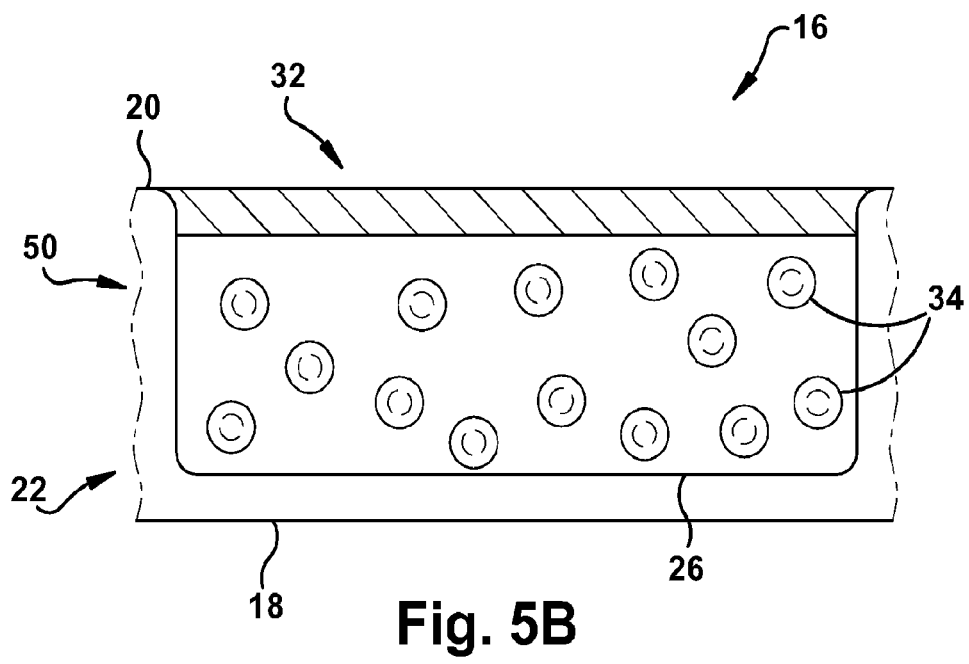
FIG. 5B is a magnified cross-sectional view showing an alternative embodiment of the reference system in FIG. 5A.

In another aspect of the present invention, the in vitro sensor 10 can include at least one reference system 16 (FIGS. 5A-B) for eliminating background responses and/or providing a standard color that acts as a reference by which the color change(s) of the sensing system 14 can be compared. At least a portion of the reference system 16 can be disposed in the second cavity 26. As shown in FIG. 5A, the reference system 16 can comprise a solid (e.g., hardened plastic), colored material 46 that is firmly seated within the second cavity 26. The material used to form the reference system 16 can be white, black, or any other color depending upon the intended application of the sensor 10. As shown in FIG. 5B, the reference system 16 can alternatively comprise at least one non-transparent microbead 34 (e.g., white or opaque) dispersed throughout a support material (e.g., PEG). In this case, the analyte-permeable membrane 32 can cover the opening 28 of the second cavity 26. It will be appreciated that depending upon the desired use of the sensor 10, the analyte-permeable membrane 32 may also cover the opening 28 of the second cavity 26 shown in FIG. 5A.

Figure 6A:
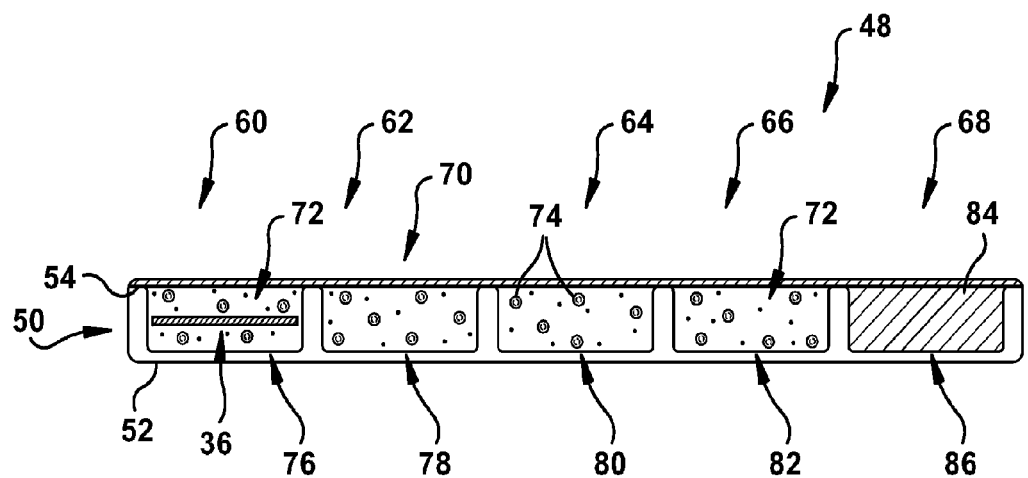
FIG. 6A is a cross-sectional view showing one example of the in vitro sensor in FIG. 1A.
Figure 6B:
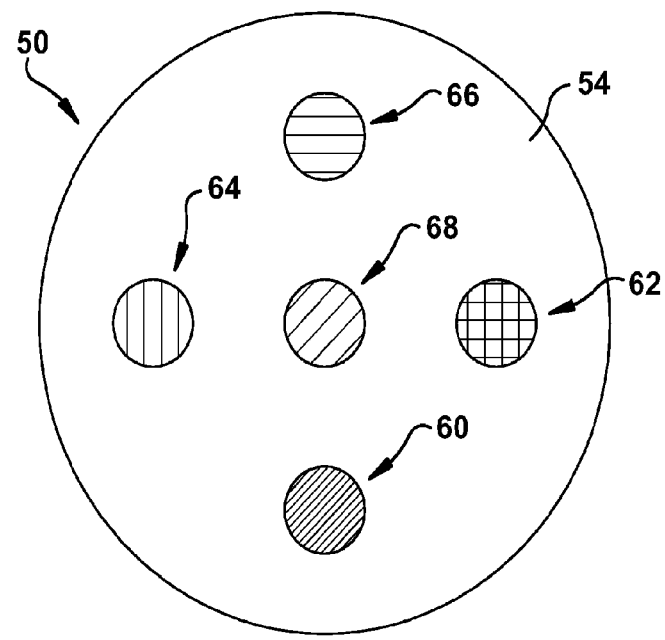
FIG. 6B is a top view of the sensor in FIG. 6A.

FIGS. 6A-B illustrate one example of the present invention comprising an in vitro sensor 48 for detecting multiple analytes in a POC environment. The sensor 48 can comprise a glass substrate 50 having a first transparent surface 52 oppositely disposed from a second surface 54. The glass substrate 50 can also include five cavities 56, each of which has an opening 58 defined by the second surface 54. The glass substrate 50 can have a substantially circular shape (FIG. 6B), and each of the cavities 56 can have a depth of about 300 µm and a diameter of about 1 mm. The diameter of the sensor 48 can be about 5 mm.

As shown in FIG. 6A, the sensor 48 can include first, second, third, and fourth sensing systems 60, 62, 64 and 66, as well as a reference system 68. The sensor 48 can also include an analyte-permeable membrane 70 comprised of polyurethane. The analyte-permeable membrane 70 can be in contact with the second surface 54 of the substrate 50 and overlay the openings 58 of each of the cavities 56. Each of the sensing systems 60, 62, 64, and 66 can also generally comprise an analyte-detection optode membrane 72 comprising, for example, about 50 mmol of chromoionophore ETH5350, about 360 mmol of an ionophore, about 55 mmol NaHFPB, and about 0.65 polyvinylchloride:bis(2-ethylhexyl)sebacate. Additionally, each of the sensing systems 60, 62, 64, and 66 can include at least one glass microbead 74 that is randomly dispersed throughout the analyte-detection optode membrane 72.

The first sensing 60 system can be at least partially disposed in a first cavity 76 of the substrate 50 and be used to detect the presence and/or concentration of glucose. The first sensing system 60 can comprise an analyte-detection optode membrane 70 (as described above), as well as an enzyme-loaded membrane 36, such as a glucose oxidase-loaded membrane.

The second sensing system 62 can be at least partially disposed in a second cavity 78 of the substrate 50 and be used to detect pH levels. The second sensing system 62 can comprise an analyte-detection optode membrane 70 comprising about 50 mmol of chromoionophore ETH5350, about 360 mmol sodium ionophore Na IV, about 55 mmol NaHFPB, and about 0.65 polyvinylchloride:bis(2-ethylhexyl)sebacate.

The third sensing system 64 can be at least partially disposed in a third cavity 80 of the substrate 50 and be used to detect the level of potassium ions. The third sensing system 64 can comprise an analyte-detection optode membrane 70 comprising about 50 mmol of chromoionophore ETH5350, about 360 mmol of a potassium ionophore (e.g., BME 44), about 55 mmol NaHFPB, and about 0.65 polyvinylchloride:bis(2-ethylhexyl)sebacate.

The fourth sensing system 66 can be at least partially disposed in a fourth cavity 82 of the substrate 50 and be used to detect the level of sodium ions. The fourth sensing system 66 can comprise an analyte-detection optode membrane 70 comprising about 50 mmol of chromoionophore ETH5350, about 360 mmol sodium ionophore Na IV, about 55 mmol NaHFPB, and about 0.65 polyvinylchloride:bis(2-ethylhexyl)sebacate.

The reference system 68 can comprise a solid, colored material 84 that is firmly seated within a fifth cavity 86 of the substrate 50. For example, the reference system 68 can comprise a solid piece of white-colored PVC.

Although the sensing systems 60, 62, 64, and 66 and the reference system 68 shown in FIG. 6B are arranged in a cross-like configuration, it should be appreciated that the sensing systems and the reference system can be arranged in any desired configuration.

Figure 7:
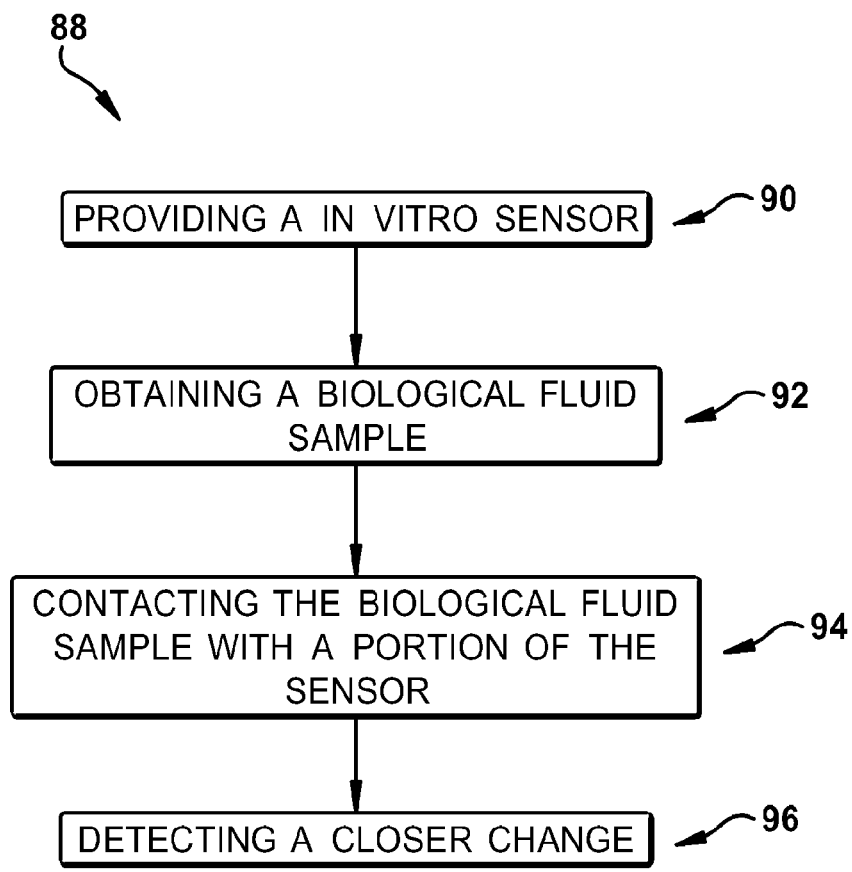
FIG. 7 is a process flow diagram illustrating a method for detecting at least one analyte or reaction product in a biological fluid sample taken from a subject at a POC according to another aspect of the present invention.

FIG. 7 illustrates another aspect of the present invention comprising a method 88 for detecting at least one analyte or reaction product in a biological fluid sample taken from a subject at a POC. As used herein, the term "subject" can refer to any warm-blooded organism including, but not limited to, human beings, rats, mice, dogs, goats, sheep, horses, monkeys, apes, pigs, rabbits, cattle, etc. The biological fluid sample can include any bodily fluid obtained from a subject (e.g., a human), such as peripheral bodily fluids, which may or may not contain cells (e.g., blood, urine, plasma, mucous, bile, pancreatic juice, supernatant fluid, and serum). The terms "POC" or "POC testing" can refer to diagnostic testing at or near the site of subject care. In one example of the present invention, POC testing can occur in a critical care environment, such as an ICU or emergency room.

As described below, the method 88 and sensor 10 of the present invention takes advantage of enzyme-based reactions, unlike the detection systems of the prior art, which typically include binding assays that exhibit several drawbacks when compared to the present invention. For example, enzyme-based reactions not only include the step of selective recognition, but also add an amplification step in the form of an enzyme-catalyzed biochemical reaction (e.g., the binding and oxidation of glucose by glucose oxidase). Conversely, binding assays are prone to interference by other molecules of similar chemical structure. Further, binding assays tend to show poor reversibility and precision after exposure to body fluids because of parasitic binding by chemically similar (but functionally different) molecules other than the intended analyte. Advantageously, the method 88 and sensor 10 of the present invention allow amplification since the detection material (e.g., an enzyme) not only provides selective recognition of an analyte molecule, but also converts the analyte into a reaction product (or products).

One aspect of the method 88 can include providing an in vitro sensor 10 at Step 90. Generally, the in vitro sensor 10 can comprise a substrate 12 having first and second surfaces 18 and 20, a sensing system 14 at least partially disposed in a first cavity 24, and a reference system 16 at least partially disposed in a second cavity 26. As discussed above, the sensing system 14 can include an analyte-permeable membrane 32, an analyte-detection optode membrane 30, and at least one non-transparent microbead 34 in contact with at least one of the analyte-permeable membrane and the analyte-detection optode membrane. The particular configuration of the sensor 10 will depend upon its intended application. For example, the number of sensing systems 14 and the composition of the analyte-permeable membrane(s) 32 and the analyte-detection optode membrane(s) 30 will depend upon the particular analyte and/or reaction product to be detected.

In one example of the method 88, the in vitro sensor 10 can be configured as shown in FIGS. 6A-B and used to detect the presence of sodium ions, potassium ions, pH, and glucose in a blood sample obtained from a subject in an ICU.

At Step 92, the biological fluid sample can be obtained from the subject using any one or combination of means known in the art. To obtain a blood sample, for instance, a syringe can be used to withdraw blood from a vein of the subject. Alternatively, if desired, a blood sample can be separated (e.g., by centrifugation) to isolate and obtain a serum sample. A blood sample can additionally or optionally obtained by lightly pricking one of the subject's fingers (e.g., with a sterile needle) and then collecting a desired volume of blood.

Figure 8:
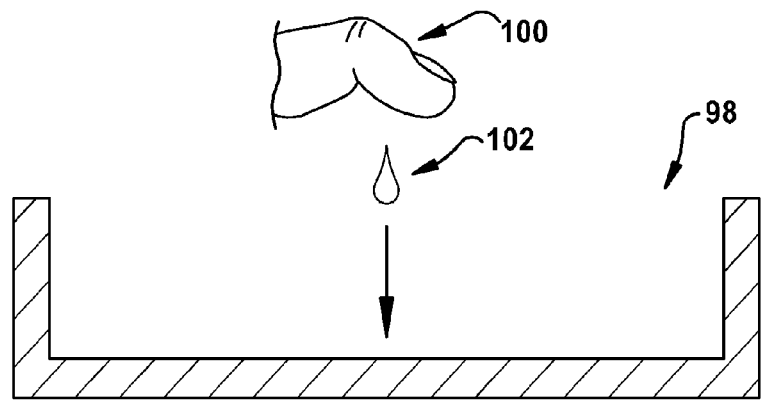
FIG. 8 is a schematic illustration showing a biological fluid sample of a subject being placed in a sample container.

In one example of the method, as little as 1 μl of blood can be collected from the subject using a hypodermic needle. Following collection of the biological fluid sample, the biological fluid sample can be placed in a sample container 98 configured to accommodate the sensor 10. The sample container 98 can comprise, for example, a plastic or glass container having a recessed portion (e.g., a well) adapted to receive the sensor 10. In one example of the method, the subject's finger 100 can be pricked (e.g., using a sterile needle) and a desired volume of blood 102 then collected in the sample container (FIG. 8).

Figure 9:
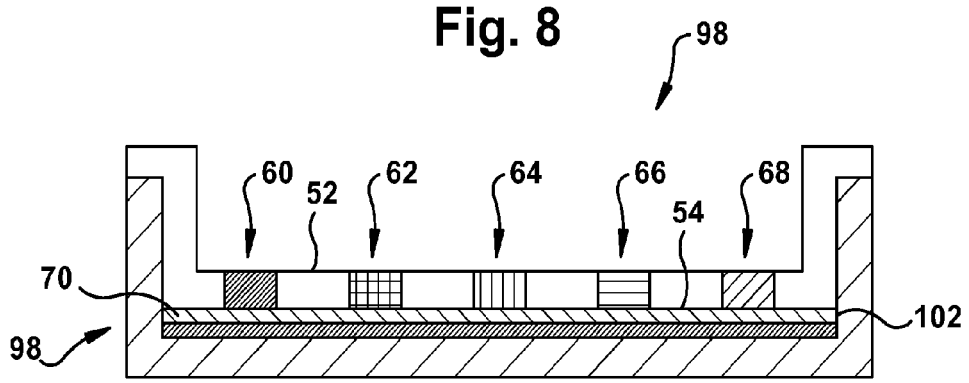
FIG. 9 is a cross-sectional view showing the sensor of FIGS. 6A-B placed on top of the biological fluid sample in FIG. 8.

At Step 94, the sensor 10 can be disposed in the sample container 98 so that the biological fluid sample contacts at least a portion of the analyte-permeable membrane 32. As shown in FIG. 9, for example, the sensor 48 can be placed in the sample container 98 so that the biological fluid sample (e.g., blood 102) is sandwiched between the bottom of the container, the second surface 54 of the substrate 50, and the analyte-permeable membrane 70. With the biological sample in contact with at least a portion of the analyte-permeable membrane 32, one or more analytes can diffuse through the analyte-permeable membrane into contact with the analyte-detection optode membrane 30. Depending upon the particular composition of the sensing system 14, the indicator material(s) and/or detection material(s) can react with (or to) the analytes and thereby elicit a color change in the sensing system.

In one example of the method 88, the sensor 48 shown in FIGS. 6A-B can be placed into a glass sample container 98 (FIG. 9). When the sensor 48 is placed in the sample container 98, blood 102 can contact the analyte-permeable membrane 70 overlaying each of the first, second, third, and fourth sensing systems 60, 62, 64 and 66. In the first sensing system 60, for example, the enzyme reaction discussed above can occur in the enzyme-loaded membrane 36 (i.e., glucose oxidase-loaded membrane). Because the enzyme reaction produces gluconic acid, the pH in the analyte-detection optode membrane 72 can reflect (and change with) the concentration of glucose in the blood sample 102. The color (i.e., the absorption spectrum) of the pH indicator dye will change due to the pH change in the membrane(s) 36 and 72.

Somewhat similar reactions can also take place in the second, third, and fourth sensing systems 62, 64 and 66. In the second sensing system 62, for instance, the indicator material in the analyte-detection optode membrane 72 can change color depending upon the concentration of hydrogen ions in the blood sample 102. Additionally, the third and fourth sensing systems 64 and 66 can change color depending upon the concentration of potassium and sodium ions, respectively, in the blood sample 102.

Figure 10:
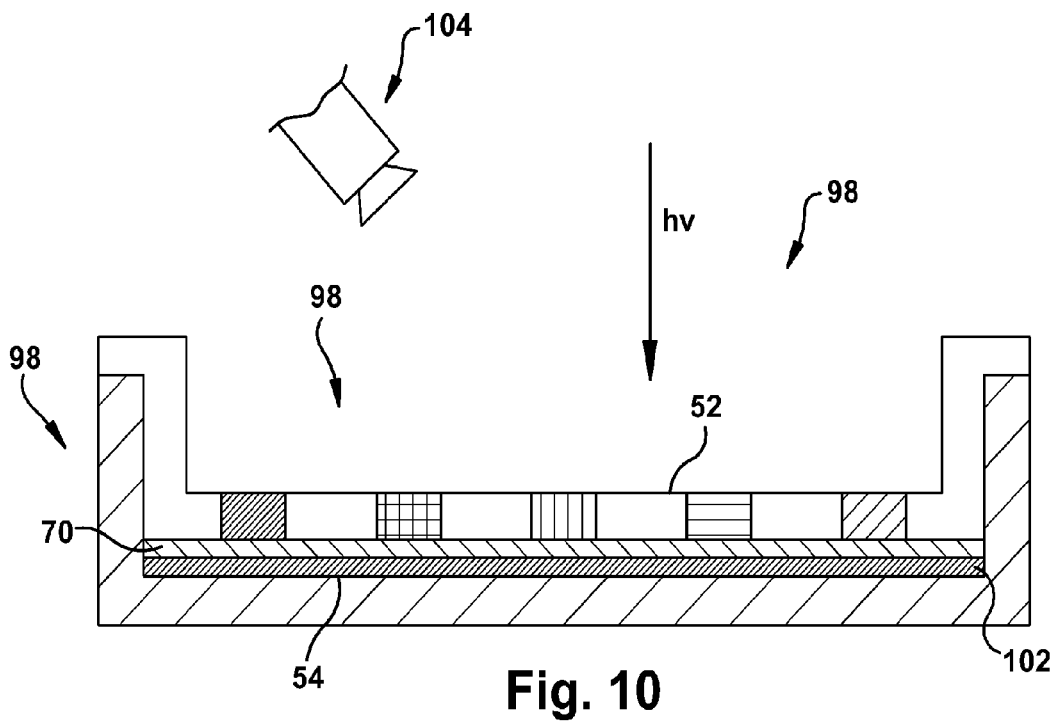
FIG. 10 is a cross-sectional view showing the application of light (hv) to the sensor in FIG. 9 and detection of at least one analyte or reaction product by a detector.
Figure 11:
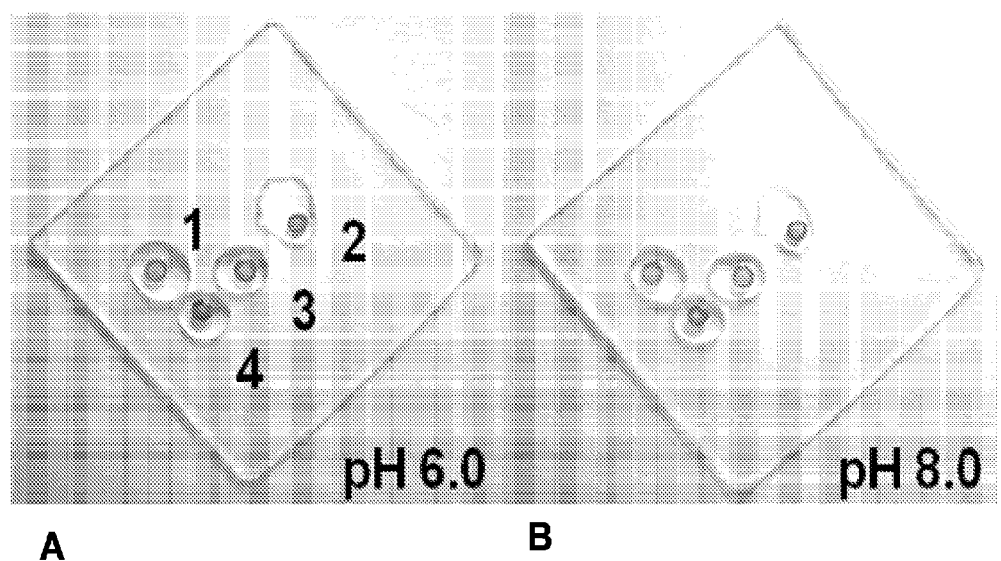
FIGS. 11A-B are a series of photographs showing two sensing spots for pH and two inert spots for reference in a glass substrate.
Figure 12:
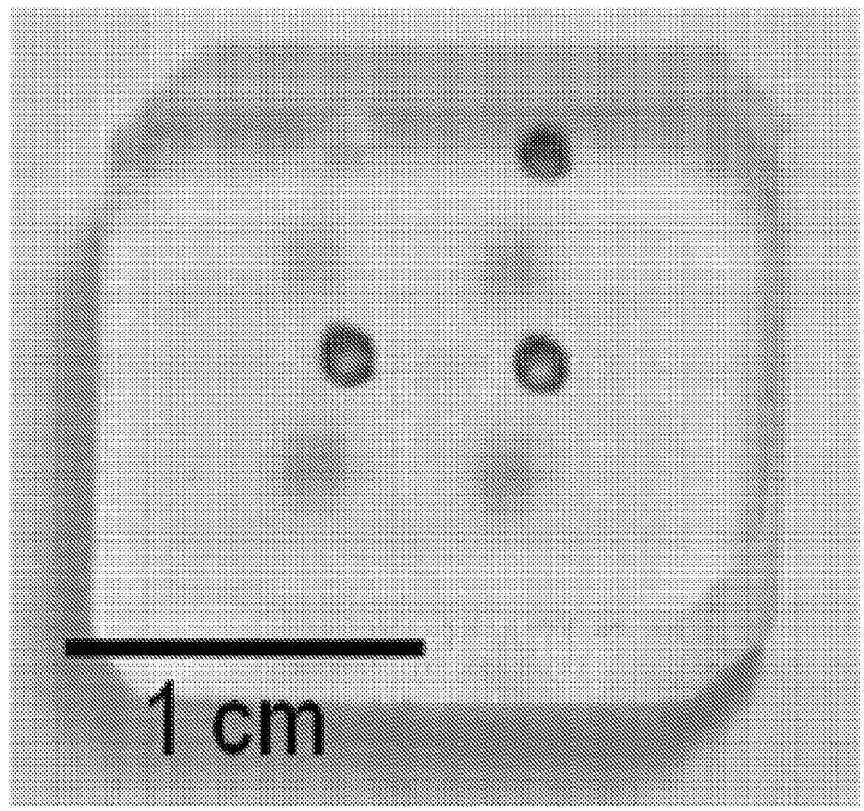
FIG. 12 is a photograph showing a thicker substrate made of plastic (in contrast to the glass substrate in FIGS. 11A-B)
Figure 13:
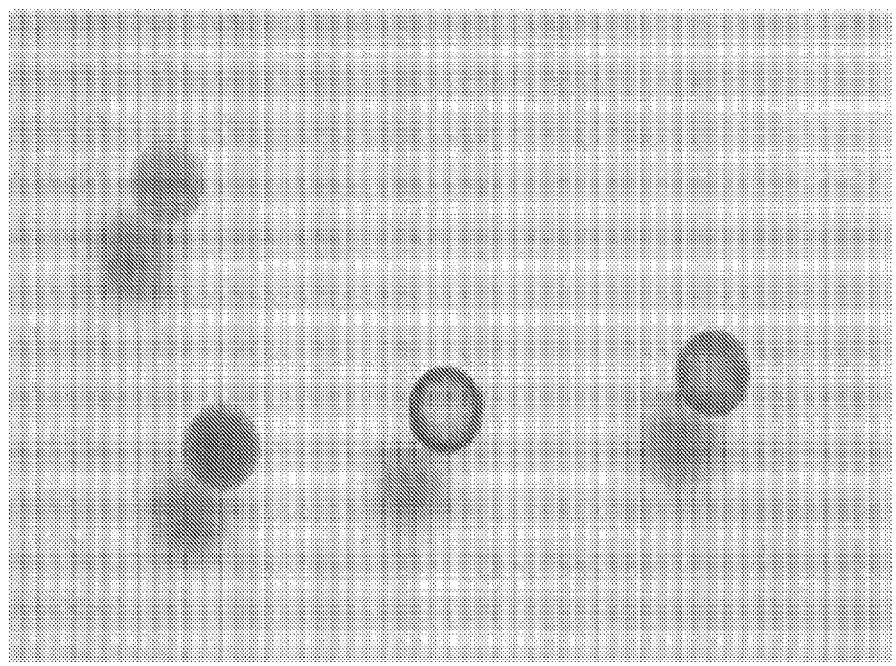
FIG. 13 is a photograph showing a sensor of the present invention having a glucose spot (left), two pH spots (right), and a white reference (above) in a glass substrate (not in solution)
Figure 14:
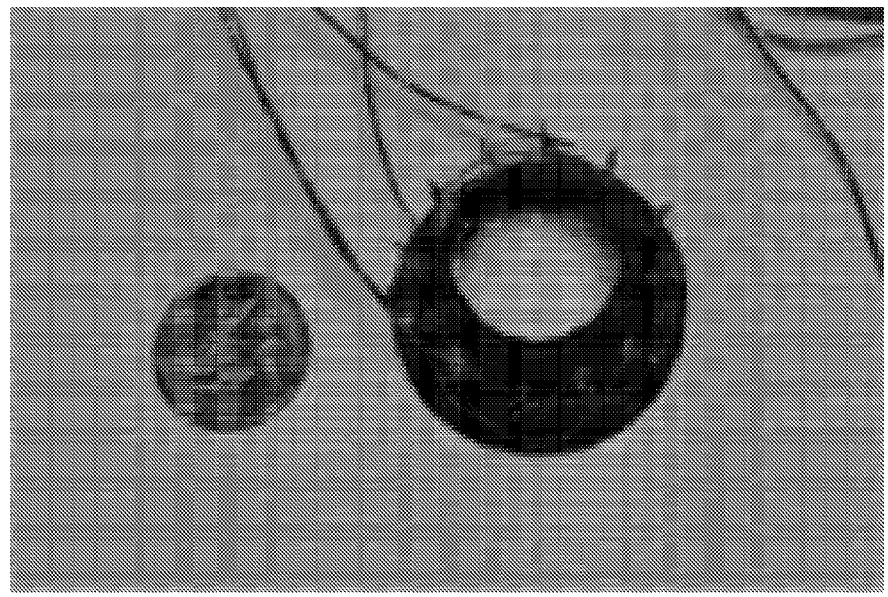
FIG. 14 is a photograph showing an LED-based (red, green and blue), charge-coupled device (CCD) for detecting color changes in the sensor of the present invention.
Figure 15:
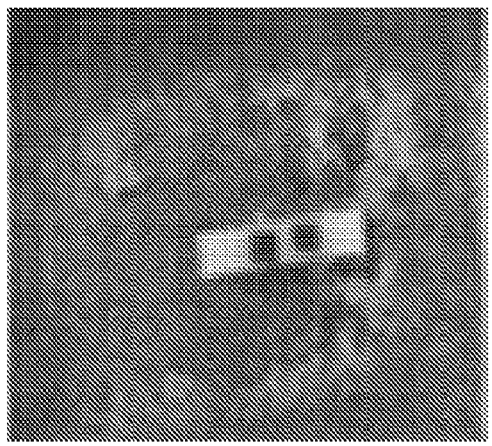
FIG. 15 is a series of grayscale photographs using the CCD in FIG. 14 highlighting color distribution at a given analyte concentration.
Figure 15:
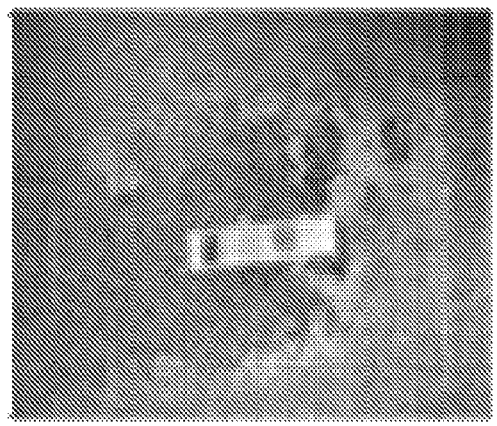
Figure 15:
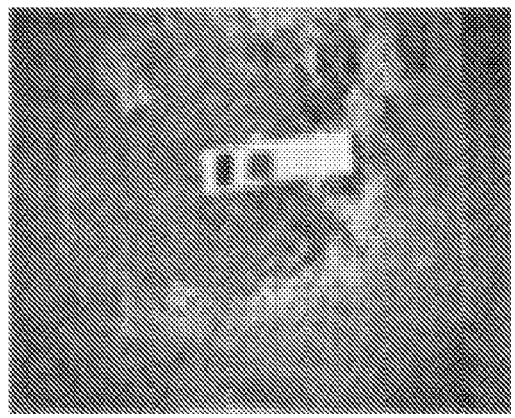

After contacting the biological fluid sample with at least a portion of the analyte-permeable membrane 32, a color change (or changes) can be detected at Step 96. As noted above, the color change can occur as a result of a changed optical property in the sensing system 14, such as a color change of an absorption dye or emission by a fluorescent dye. The color change can be detected by a detector 104 (FIG. 10). The detector 104 can detect color changes that occur and determine the analyte concentration by reference to calibration charts, look-up tables, or the like. The detector 104 can include any type of scanning device, such as a charge-coupled device (CCD) (e.g., CCD camera) or spectrophotometer that is capable of registering the wavelength of light emitted by each of the sensing systems 14 and/or its intensity. In one example of the method 88, the detector 104 can comprise a color CCD camera that automatically recognizes the components of the sensor 10, such as the sensing systems 14 and reference system 16 via image processing.

Alternatively, the detector 104 can include a human eye. Visual examination generally permits a qualitative or semi-quantitative assessment rather than a quantitative assessment of analyte concentration. In many cases, however, such an assessment is sufficient for subject management.

In one example of the present invention, the indicator material (e.g., a pH sensitive dye) immobilized on (or in) the analyte-detection optode membrane 30 can change color (i.e., absorption wavelength) depending upon the concentration of analyte species being monitored. The color can be recognized by the detector 104 using a light source (which may be integral with the detector) and a suitable color measuring device, such as spectrophotometer with a digital data processing unit. For example, a spectrophotometer can detect the absorbance of light at one or more wavelengths or wavelength ranges where the indicator material absorbs. With increasing concentration of the analyte, the absorbance at the selected wavelength either increases or decreases, depending on whether the absorbance is due to a protonated or an unprotonated form of the indicator material. The absorbance can then be correlated with the concentration of glucose, for example, using an algorithm or look-up table based on precalibration with solutions of known glucose concentrations covering the range of concentrations to be measured.

Where a CCD camera or other similar device is used to detect the color change, it will be appreciated that the detector 104 can be in communication with a computer processor (not shown) so that ratiometric techniques (e.g., spectral shape recognition to identify "color") can be used for precise, quantitative analyte monitoring. In a more advanced detection system, for example, shape recognition can be used. In such a system, the signal that carries the information sought for is the color of the different sensing spots. It is therefore represented, in physical terms, in the form of a spectrum. This may be a reflected, back-scattered, or even a transmittance spectrum, but an important feature is that color for a detecting instrument is equivalent to a spectrum. More precisely, it is the shape of the spectrum which is of concern and, thus, it is independent of intensity.

This is not the case for other existing approaches. For example, electrochemical methods transduce concentration into current intensity, which is a single variable. Fluorescence-based methods transduce concentration into fluorescence intensity, which is also a single variable. In the present method, the actual color indicates concentration, meaning that concentration is transduced into the shape of a spectrum. This spectrum may be transmitted or reflected or back-scattered intensity, or some derived variable like absorbance, as a function of wavelength or frequency of light. The spectrum can be acquired by scanning through a given range of light wavelengths or frequencies. The result is a function consisting of a number of value pairs, such as intensity and frequency pairs. The number of these pairs can be 3, 4, or even hundreds, depending on resolution and range. Thus, one concentration value is represented by a large number of independent data points. This means a high degree of redundancy, which can be used to improve greatly the statistical quality and reliability of the concentration determined. This is in contrast with intensity-based techniques, where one value is obtained from just one other value, i.e., the concentration. To make use of the large amount of information available in the form of a spectrum, the shape can be used for calibration of the sensor 10 versus concentration, as well as for retrieving unknown concentrations from the calibration.

There are a variety of methods for quantifying the spectrum shape. These include pattern recognition approaches, factor analysis, and curve fitting techniques. In one example of the method 88, shape is identified with the direction of a vector constructed from the data pairs that make up the spectrum in a multidimensional space. This makes it possible to identify concentrations using similarity in the direction of the actual data vector and that of some standard or calibration-based vector. Closeness of the two directions is ensured when the angle between two such vectors is small and close to zero.

The advantages of using a shape analysis can include: independence of actual optical path lengths which tend to affect intensity but do not affect spectrum shape; a great degree of independence from random noise, since it is sufficient to identify the overall shape of the spectrum (i.e., its lowest frequency components to identify the concentration that caused it); extreme robustness of the approach in terms of high immunity from potential error sources such as random and some non-random errors; and the potential for self-testing is ensured because it is impossible or unlikely that shapes can be readily recognized. These advantages are generally unavailable with conventional evaluation techniques.

In one example of the present invention, a color CCD can be used to detect the concentration of glucose, pH, potassium, and sodium. To detect the concentration of glucose, for example, image processing can be used to subtract background between the spectra of the first sensing system 60 and the reference system 68. Software in a computer processor can carry out subtraction of the background using information from the reference system 68 and provide a measure of the glucose concentration (or other analytes). The CCD camera can detect light emitted at two or more wavelengths (e.g., at least ten wavelengths) within the range emitted/absorbed by the indicator material or other color-producing material. In this way, the software is able to recognize the shape of the wavelength distribution curve (e.g., a plot of intensity vs. wavelength) from the relationship between the intensities of the wavelengths detected, which is a constant for the particular color and, thus, identify it with the color of the light being emitted/absorbed. This recognition of color, rather than intensity of the light from the sensing element, reduces the influence of variables, such as optical path length on the detection of the analyte.

The system is particularly useful where there is a plurality of sensing systems 14, each one generating a color change at a different analyte concentration. The software can then provide a simple yes/no detection for each sensing system 14, depending upon whether a color is generated. This is largely independent of optical path length and other factors affecting light intensity, such as the wavelength or intensity of the ambient light or other light incident on the sensing system 14. The number of sensing systems 14 changing color can then be used as a measure of analyte concentration.

Unlike other POC testing devices and methods, the present invention advantageously provides low cost, reversible optode technology that translates analyte concentrations into colors that can be detected using simple devices (e.g., LED and photodiodes). The present invention is tunable to different analytes so that more analytes can be detected depending upon the clinical need of the subject. Since the sensor 10 of the present invention is reversible and requires neither power nor reagents to operate, a single sensor can be re-used many times so that an individual subject's entire period of care (e.g., in the ICU) can be covered with just one sensor. Thus, unlike conventional POC analyte test strips, the present invention provides a real-time snapshot of the overall metabolic status of a subject from a single biological fluid sample at the POC.

The following examples are for the purpose of illustration only and are not intended to limit the scope of the claims, which are appended hereto.

Example 1

Calibrations of HEMA-Based pH Sensors in Serum and Blood Sensor Construction

Figure 16:
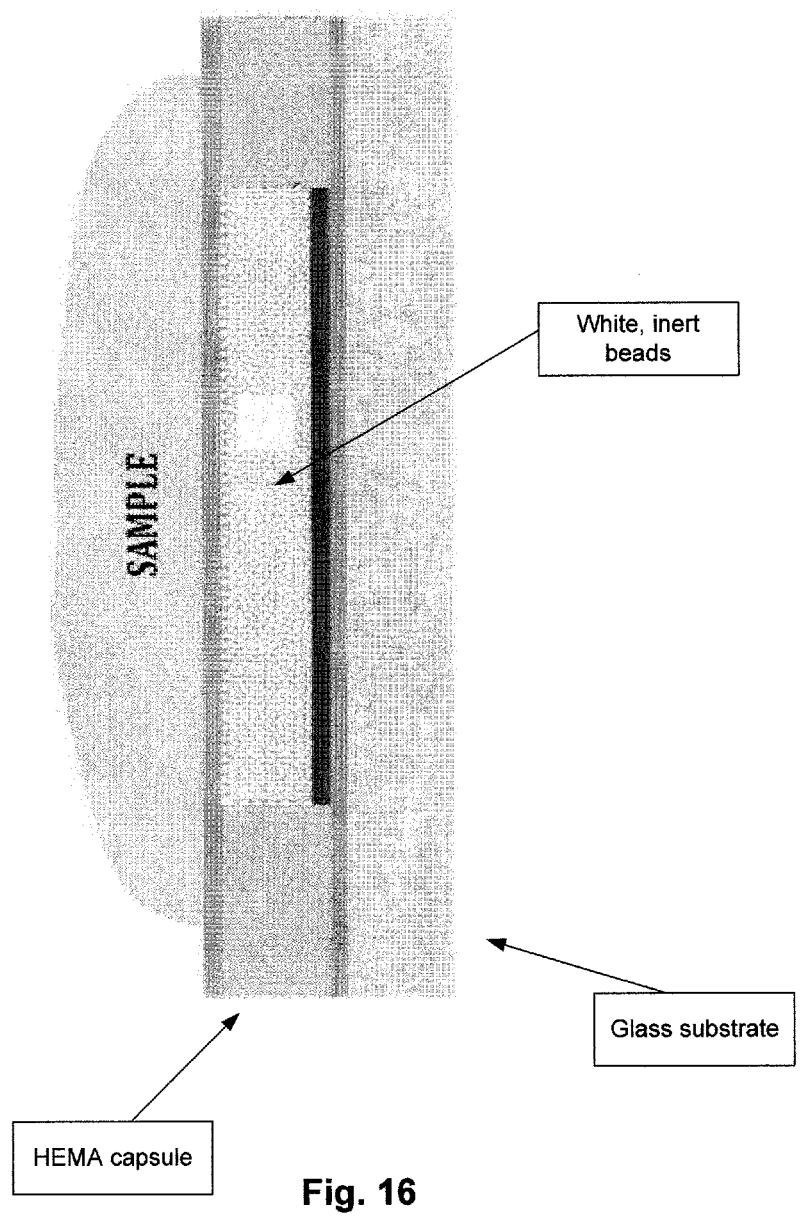
FIG. 16 is a schematic illustration showing a pH sensor constructed in accordance with another aspect of the present invention.

As shown in FIG. 16, a pH sensor having the following components was constructed as follows: a glass substrate (inert, transparent and impermeable); a 3-layered HEMA capsule; and white inert beads for suppressing sample optical interference layered on top of the sensing membrane. The HEMA capsule had the following configuration: a layer for attachment to the glass substrate (~17 μm thick); a membrane capsule layer (~150 μm thick); and a thin permeable layer for the analyte membrane and for protecting the structure against biofouling. The membrane composition had the following components as well: chromoionophore ETH350 (50 mmol); sodium ionophore Na IV (360 mmol); ionic site NaHFPB (55 mmol); and PVC:DOS (0.65).

In all cases, pH was adjusted by adding small aliquots of KOH or HCl to serum or blood.

Calibration of HEMA-Based pH Sensor in Serum

Figure 17:
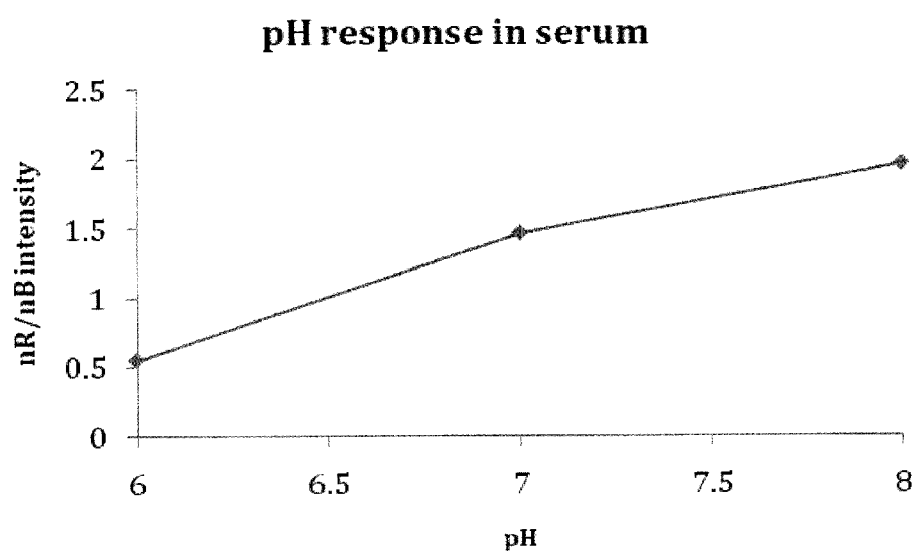
FIG. 17 is a graph of pH vs. nR/nB intensity showing pH response in serum using the sensor in FIG. 16.
Figure 18:
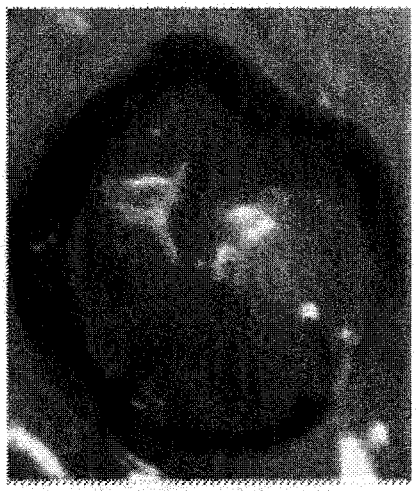
FIG. 18 is a series of images showing the pH response of the sensor in FIG. 16 in serum (a: pH 6; b: pH 7; c: pH 8)
Figure 18:
Figure 18:
Figure 19:
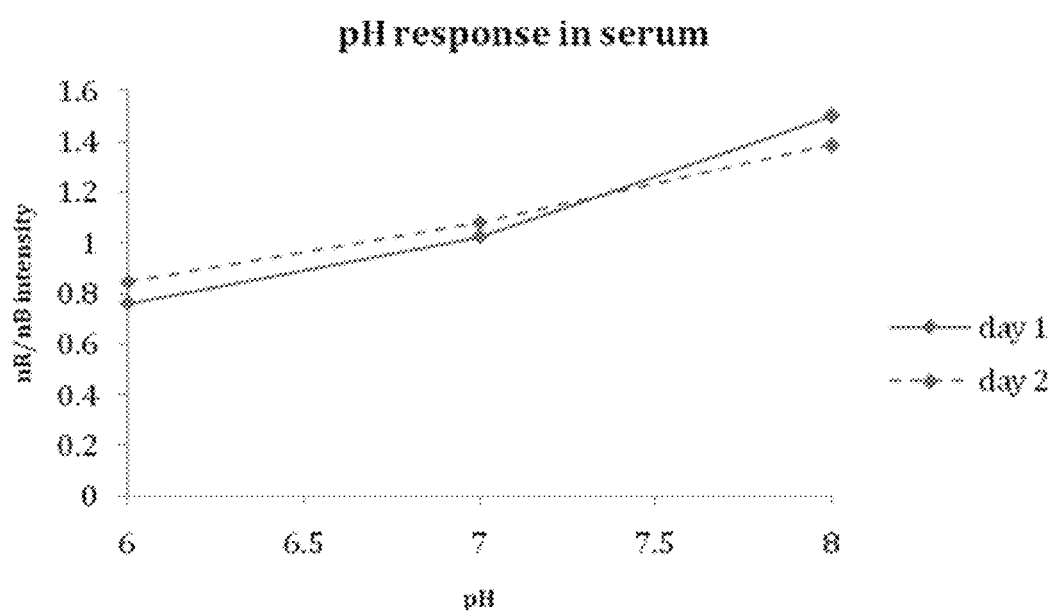
FIG. 19 is a graph of pH vs. nR/nB intensity showing pH response in serum using the sensor in FIG. 16 over the course of two days.

Serum calibrations for pH sensors: KOH or HCl was added to fetal bovine serum (FBS) to adjust pH to desired values. Sensors were placed in FBS solutions for 10 minutes. FIG. 17 shows the pH response to FBS of the sensors. FIG. 18 shows an actual pH sensing spot in FBS solutions. FIG. 19 shows the pH response to FBS of sensor after 1 and 2 days exposure. All calibrations use ratio of normalized red:normalized blue color intensity.

Calibration of HEMA-Based Sensor in Blood

Figure 20:
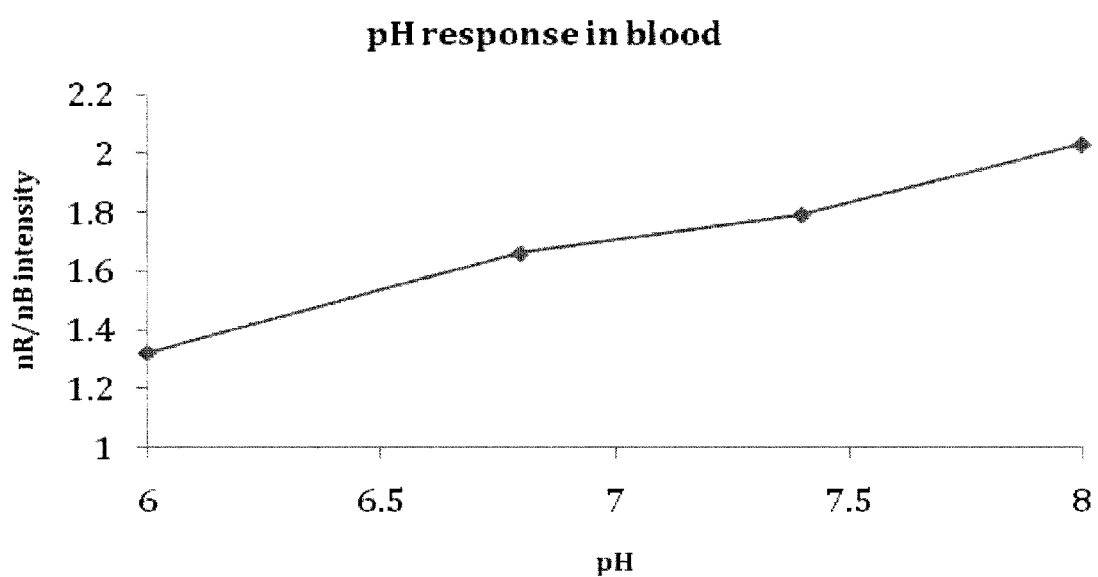
FIG. 20 is a graph of pH vs. nR/nB intensity showing pH response in blood using the sensor in FIG. 16.
Figure 21:
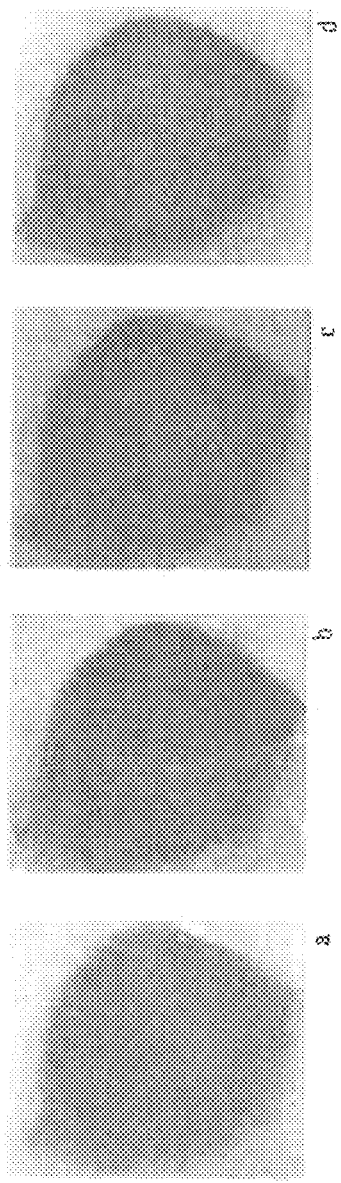
FIG. 21 is a series of images showing the pH response of the sensor in FIG. 16 in blood (a: pH 6; b: pH 6.8; c: pH 7.4, d: pH 8)
Figure 22:
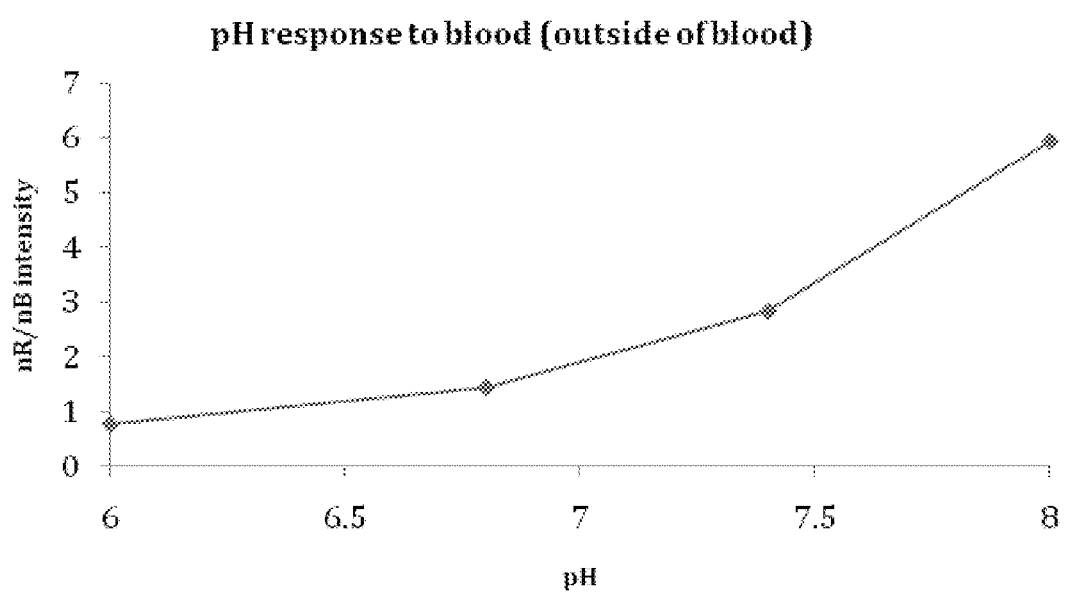
FIG. 22 is a graph pH vs. nR/nB intensity showing pH response in blood (outside of blood) using the sensor in FIG. 16.
Figure 23:
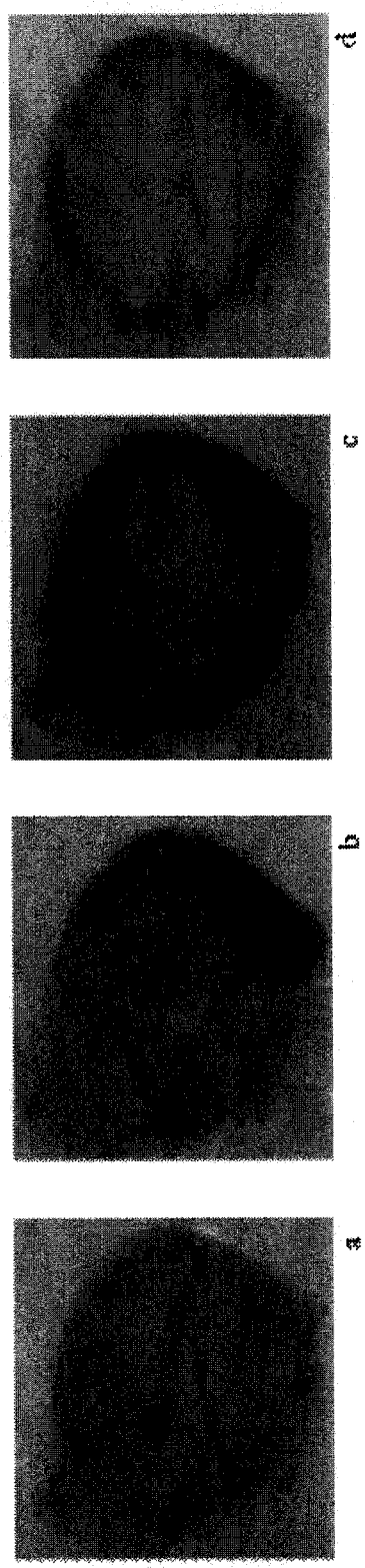
FIG. 23 is a series of images showing the pH response of the sensor in FIG. 16 immediately after the sensor was removed from the blood sample (a: pH 6; b: pH 6.8; c: pH 7.4, d: pH 8)

Human blood calibrations for pH sensors: 1× human blood sample was added to 10× phosphate buffered saline (PBS). KOH or HCl was initially added to PBS to adjust pH to desired values. Sensors were placed in human blood+PBS solutions for 10 minutes. FIG. 20 shows the response of sensors while still in blood. FIG. 21 shows the pH sensing spot in blood sample at various pH levels. FIG. 22 shows the pH response of sensors immediately after sensor was removed from blood sample. FIG. 23 shows pH sensing spot immediately after sensor was removed from blood sample. All calibrations use ratio of normalized red:normalized blue color intensity.

Example 2

Calibrations of HEMA-Based Glucose-Sensors in Serum and Blood

Figure 24:
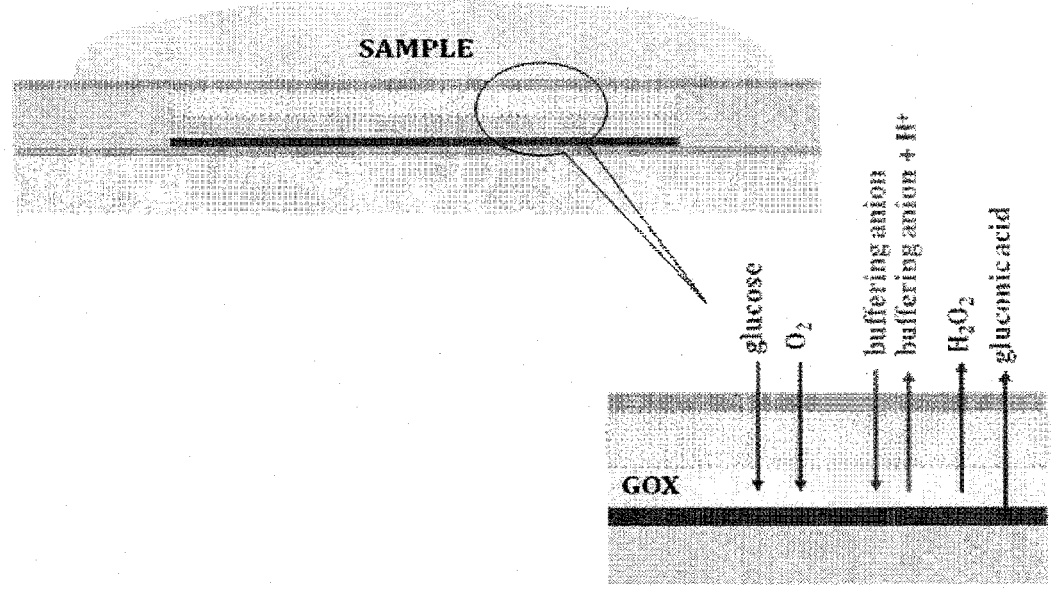
FIG. 24 is a schematic illustration showing a glucose sensor constructed in accordance with another aspect of the present invention.

A glucose sensor was constructed as shown in FIG. 24. The glucose sensing capsule contained a pH sensing membrane and a GOX solution. 2 mg of GOX was dissolved in 200 μL of PBS. 1 μL of GOX solution was added to each glucose sensing capsule. The sensor remained exposed to air overnight to allow for formation of the GOX membrane.

Figure 25:
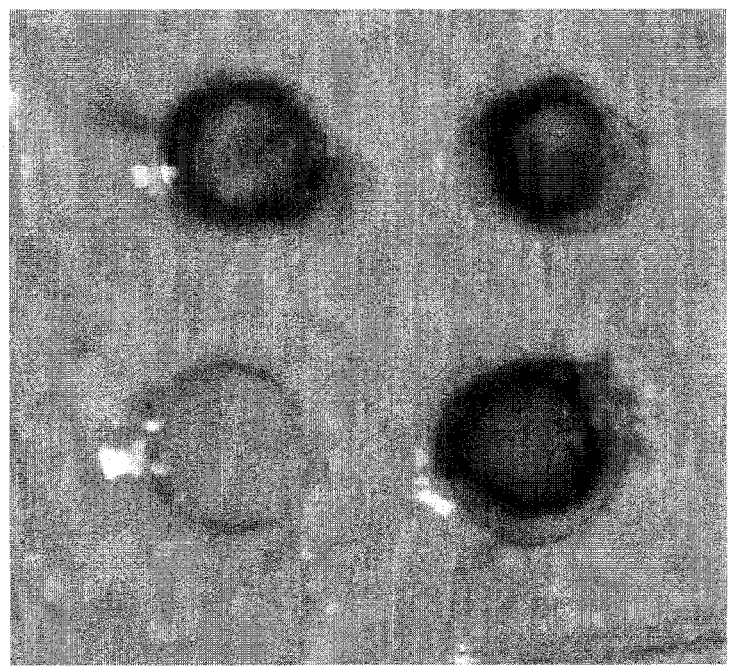
FIG. 25 is an image of a sensor array with two glucose sensors as shown in FIG. 24 (top), a white reference spot (bottom, L), and a pH sensing spot (bottom, R)

Sensors were made consisting of a pH sensing spot, 2 glucose sensing spots, and a white optical reference to create a multi-parameter sensing array. The sensor is composed of 3-layer HEMA membrane+glass substrate, as described in Example 1. FIG. 25 shows the sensing array.

In all cases, glucose level was adjusted by adding small weights of glucose monohydrate to serum or human blood.

Calibration of HEMA-Based Glucose Sensor in Serum

Figure 26:
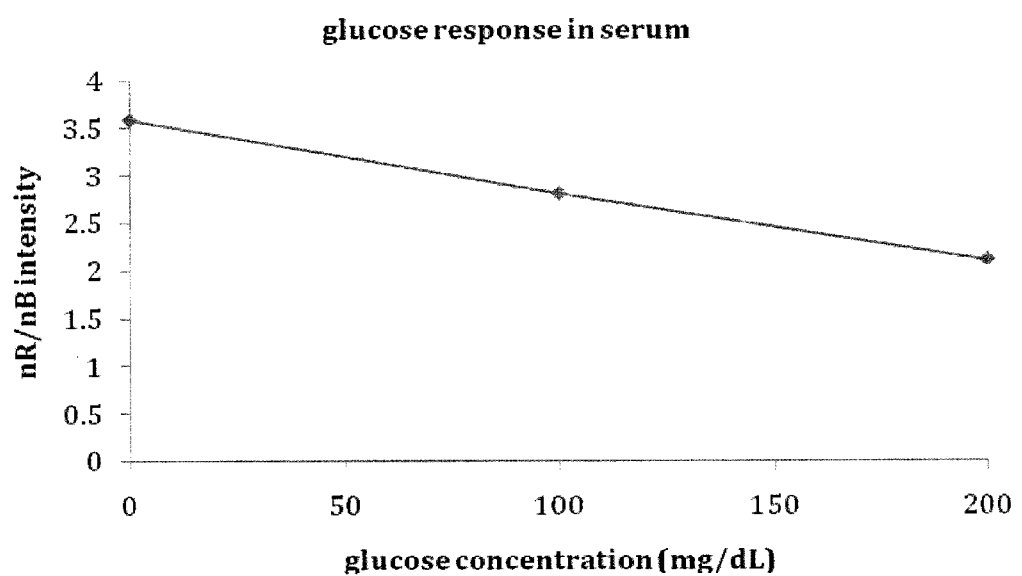
FIG. 26 is a graph of glucose concentration (mg/dL) vs. nR/nB intensity showing glucose response in serum of the sensor in FIG. 24.
Figure 27:
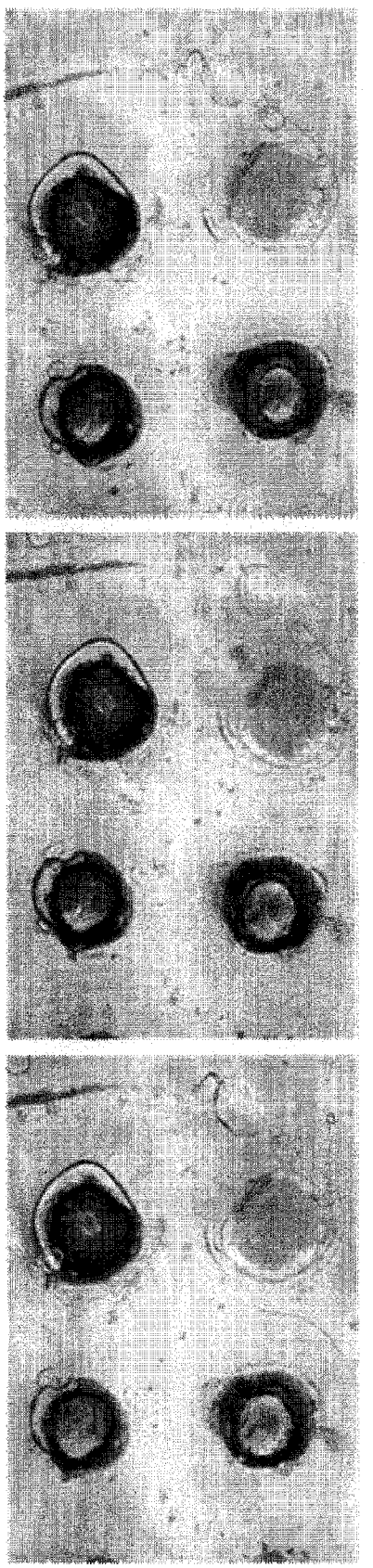
FIG. 27 is a series of images showing a multi-parameter sensing array with two glucose sensors as shown in FIG. 24 (L, top and bottom), response in serum to varying glucose concentrations (a: 0 mg/dL, b: 100 mg/dL, c: 200 mg/dL)

Serum calibrations for glucose sensors: glucose monohyrdrate was added to FBS to adjust to desired glucose levels. Sensors were placed in FBS solutions for 10 minutes. FIG. 26 shows the glucose response to FBS of the sensors. FIG. 27 shows an actual glucose sensing spot in FBS solutions. All calibrations use ratio of normalized red:normalized blue color intensity.

Calibration of HEMA-Based Glucose Sensor in Blood

Figure 28:
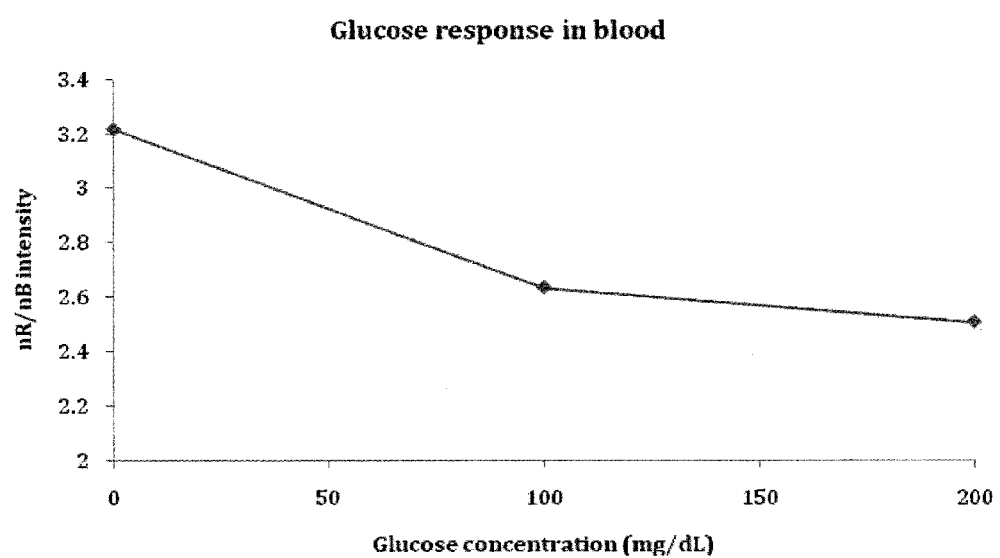
FIG. 28 is a graph of glucose concentration (mg/dL) vs. nR/nB intensity showing glucose response in blood of the sensor in FIG. 24.
Figure 29:
FIG. 29 is a series of images showing the glucose sensor (FIG. 24) response in blood with varying glucose concentrations (a: 0 mg/dL, b: 100 mg/dL, c: 200 mg/dL)
Figure 30:
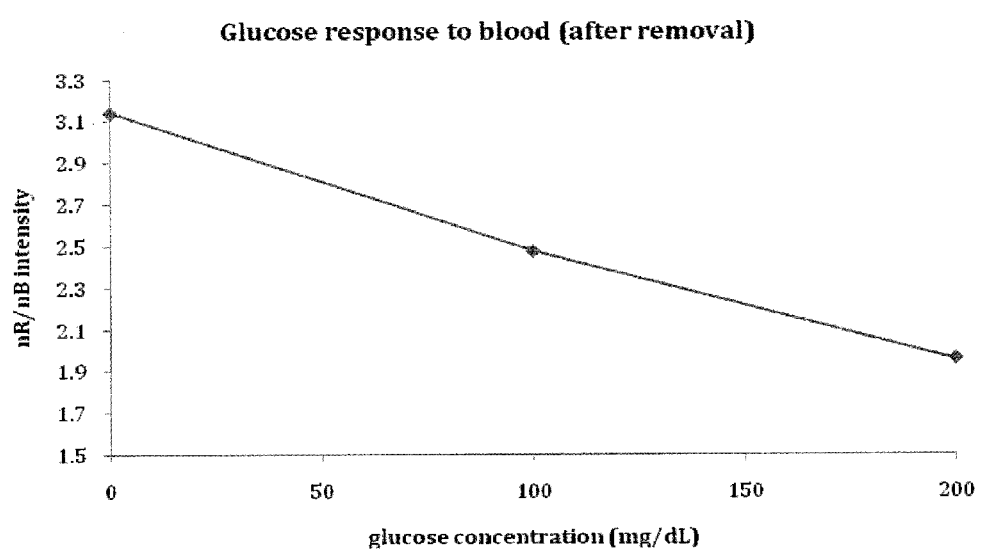
FIG. 30 is a graph of glucose concentration (mg/dL) vs. nR/nB intensity showing glucose response in blood immediately after the sensor (FIG. 24) is removed from the blood.

Human blood calibrations for glucose sensors: 1× volume human blood sample was added to 10× volume PBS. Glucose monohyrdrate was added to PBS to adjust to desired glucose levels. Sensors were placed in human blood+glucose solutions for 10 minutes. FIG. 28 shows the response of sensors while still in blood. FIG. 29 shows the glucose sensing spots in blood sample at various pH levels. FIG. 30 shows the glucose response of sensors immediately after sensor was removed from blood sample. FIG. 31 shows pH glucose spot immediately after sensor was removed from blood sample. All calibrations use ratio of normalized red:normalized blue color intensity.

From the above description of the invention, those skilled in the art will perceive improvements, changes, and modifications. Such improvements, changes, and modifications are within the skill of the art are intended to be covered by the appended claims.

Having described the invention, the following is claimed:

1. An in vitro sensor for point-of-care (POC) detection of at least one analyte or reaction product, said sensor comprising:
   an inert, impermeable substrate including a first transparent surface oppositely disposed from a second surface and first and second cavities, each of said first and second cavities defining an opening at said second surface;
   a sensing system disposed in at least a portion of said first cavity, said sensing system comprising an analyte-detection optode membrane, an analyte-permeable membrane, and a plurality of non-transparent microbeads associated with at least one of said analyte-detection optode membrane and said analyte-permeable membrane, said analyte-permeable membrane being layered upon said analyte-detection optode membrane and covering said opening of said first cavity; and
   a reference system disposed in at least a portion of said second cavity.

2. The sensor of claim 1, wherein at least a portion of said substrate is formed from one or more of polymethylmetacrylate, 2-hydroxyethyl methacrylate, and glass.

3. The sensor of claim 1, wherein at least a portion of said substrate is darkened.

4. The sensor of claim 1, wherein said opening of said at least one cavity has a diameter of about 1 mm and a depth of about 300 µm.

5. The sensor of claim 1, wherein said analyte-detection optode membrane includes at least one indicator material that undergoes a color change in response to the analyte or reaction product.

6. The sensor of claim 5, wherein said analyte-detection optode membrane includes at least one detection material.

7. The sensor of claim 1, wherein said analyte-permeable membrane is transparent.

8. The sensor of claim 1, wherein said analyte-permeable membrane is permeable to select molecules.

9. The sensor of claim 8, wherein said analyte-permeable membrane excludes at least one of anions, lipids and proteins.

10. The sensor of claim 1, wherein said analyte-permeable membrane has a multi-layered comprising:
    an outermost layer that is in contact with a biological fluid sample;
    a middle layer for regulating and limiting the diffusion of molecules into said at least one cavity; and
    a negatively-charged inner layer that is in contact with said analyte-detection optode membrane.

11. The sensor of claim 1, wherein said plurality of non-transparent microbeads is dispersed within at least one of said analyte-detection optode membrane and said analyte-permeable membrane.

12. The sensor of claim 1, wherein said plurality of non-transparent microbeads comprises a layer disposed between said analyte-detection optode membrane and said analyte-permeable membrane.

13. A method for detecting at least one analyte or reaction product in a biological fluid sample taken from a subject at a POC, said method comprising the steps of:
    providing an in vitro sensor comprising a substrate having first and second cavities, a sensing system at least partially disposed in the first cavity, and a reference system at least partially disposed in the second cavity, the sensing system comprising an analyte-detection optode membrane, an analyte-permeable membrane, and a plurality of non-transparent microbeads associated with at least one of the analyte-detection optode membrane and the analyte-permeable membrane, the analyte-permeable membrane being layered upon the analyte-detection optode membrane and covering the opening of the first cavity;
    obtaining the biological fluid sample from the subject;
    contacting the biological fluid sample with at least a portion of the analyte-permeable membrane; and
    detecting a color change within the sensing system.

14. The method of claim 13, wherein said contacting step further comprises the steps of:
    providing a sample container configured to accommodate the sensor;
    placing the biological fluid sample in the sample container; and
    placing the sensor in the sample container so that the biological fluid sample contacts the at least a portion of the analyte-permeable membrane.

15. The method of claim 13, wherein said detecting step further comprises the step of using a charge-coupled device to detect the color change.

16. The method of claim 15 further comprising the step of transforming the detected color change into a quantitative reading.

17. The method of claim 13, the POC being a critical care environment.

18. The method of claim 17, the critical care environment being an intensive care unit.

* * * * *